(12) United States Patent
Kishii et al.

(10) Patent No.: US 6,518,572 B1
(45) Date of Patent: *Feb. 11, 2003

(54) INFRARED MICROSCOPIC SPECTRUM ANALYSIS APPARATUS AND METHOD FOR ANALYSIS OF RECORDING MEDIA USING THE SAME

(75) Inventors: Noriyuki Kishii, Kanagawa (JP); Takahiro Kamei, Kanagawa (JP); Ken Kobayashi, Kanagawa (JP)

(73) Assignee: Sony Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/457,131

(22) Filed: Dec. 9, 1999

(30) Foreign Application Priority Data

Mar. 25, 1999 (JP) .......................................... 11-081196

(51) Int. Cl.$^7$ .............................................. G01N 21/35
(52) U.S. Cl. ................................................ 250/339.08
(58) Field of Search ......................... 250/339.08, 341.8; 356/445

(56) References Cited

U.S. PATENT DOCUMENTS

| | | | | |
|---|---|---|---|---|
| 3,778,308 A | | 12/1973 | Roller et al. ................. 428/421 |
| 4,765,188 A | * | 8/1988 | Krechmery et al. ........... 73/708 |
| 5,048,970 A | * | 9/1991 | Milosevic et al. ........... 356/445 |
| 5,106,196 A | * | 4/1992 | Brierley ....................... 356/445 |
| 5,176,943 A | * | 1/1993 | Woo ........................... 428/64.4 |
| 5,210,418 A | * | 5/1993 | Harrick et al. ......... 250/339.07 |
| 5,262,845 A | * | 11/1993 | Milosevic et al. ........... 356/445 |
| 5,286,534 A | * | 2/1994 | Kohler et al. ................ 427/577 |
| 5,409,738 A | * | 4/1995 | Matsunuma et al. ......... 427/502 |

\* cited by examiner

Primary Examiner—Constantine Hannaher
Assistant Examiner—Shun Lee
(74) Attorney, Agent, or Firm—Sonnenschein, Nath & Rosenthal

(57) ABSTRACT

A microscopic analysis apparatus for analysis of infrared single beam spectrum is composed of an interference light source unit, a measuring unit, and a signal processing unit. The measuring unit is configured such that a semi-spherical prism made from germanium, an incident angle varying device composed of a pair of opposed parabolic mirrors, and a detector for sensing light totally reflected from the surface of a sample are provided in an enclosed sample chamber. According to the method using the analysis apparatus, a profile of a concentration of an organic lubricant contained in a sample in the depth direction of the sample is measured by bringing the surface on the magnetic layer formation side of a floppy disk as the sample into press-contact on the bottom surface of the prism at a low pressure, scanning an incident angle of an infrared light ray on the prism, and analyzing the spectrum of the infrared light ray totally reflected from the surface of the sample.

20 Claims, 19 Drawing Sheets

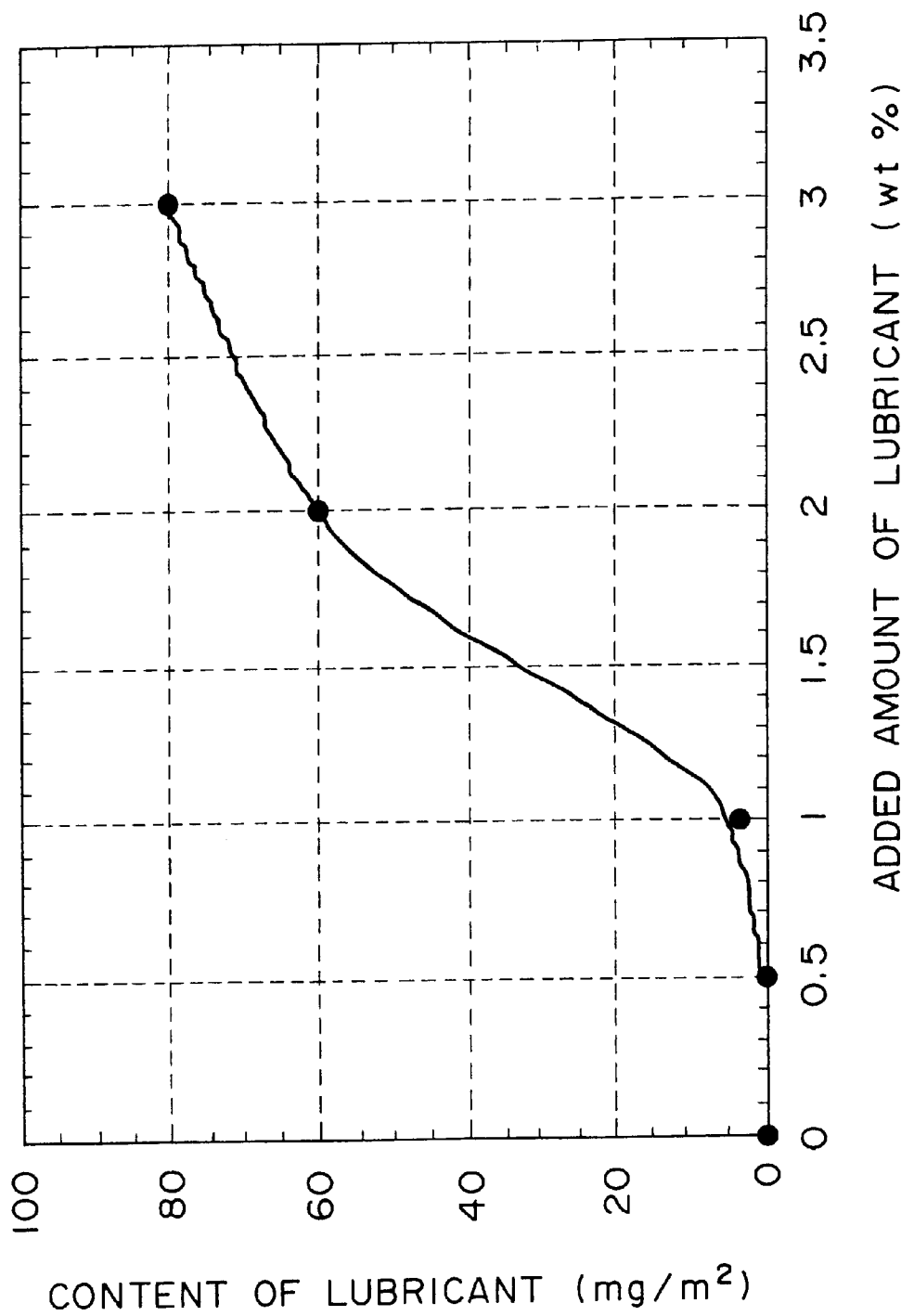
F I G. 12

INFRARED MICROSCOPIC SPECTRUM ANALYSIS APPARATUS AND METHOD FOR ANALYSIS OF RECORDING MEDIA USING THE SAME

BACKGROUND OF THE INVENTION

The present invention relates to an infrared microscopic/FT-IR (Fourier transform infrared spectrometer) apparatus based on an attenuated total reflection method, in which a surface portion of a sample is analyzed by bringing a prism into press-contact with the surface of the sample, making an infrared light ray incident on the prism at an arbitrary angle, and analyzing the spectrum of the infrared light ray totally reflected from the surface of the sample by the FT-IR apparatus, and a method for analysis of high density recording media using the apparatus.

Magnetic recording media are widely utilized as an audio tape, a video tape, a back-up data cartridge, a floppy disk, and a hard disk. In particular, recently, examination has been actively made to shorten a recording wavelength or realize high density recording by adopting a digital recording method or the like, and it has been required to develop magnetic recording media excellent in electromagnetic transformation characteristic.

With respect to a coating type magnetic recording medium having been mainly used at present, it has been examined to make a magnetic layer thin for reducing a self-demagnetization loss upon recording, thereby improving the electromagnetic transformation characteristic. In recent years, various coating methods have been proposed from the viewpoint of thinning of the magnetic layer.

In general, the surface of a recording medium is smoothened to minimize a spacing loss upon recording/reproducing. In high density recording, since a recording wavelength used is short, recording tends to be affected by the surface roughness, and therefore, the control of the surface roughness is particularly important.

In this way, with increased output of a magnetic tape, it is required to significantly enhance the smoothness of the surface of a magnetic layer, and correspondingly the substantial contact area of the magnetic layer with a sliding member such as a magnetic head or a guide roller becomes large. As a result, the friction coefficient between the magnetic layer and the sliding member becomes large, and thereby an adhesion phenomenon (so-called sticking) therebetween is easy to occur. This causes a problem such as the lack of running characteristic and durability of the magnetic tape.

To solve the above problem, it has been examined to use various organic lubricants. For example, attempts have been made to add higher fatty acid or its ester in or on the magnetic layer of the magnetic recording medium for reducing the friction coefficient between the magnetic layer and the sliding member.

At the present time, however, as a method of quantitatively measuring the amount of lubricant adhering on the surface of the magnetic recording medium or contained in the medium, there has been known only a method of analyzing the amount of the lubricant by extracting the lubricant by. using solvent. According to such an extraction method, only a lubricant dissolved in a solvent (hexane or toluene) can be measured, and it takes a lot of time to measure the amount of the lubricant. For this reason, it has been very difficult to control the added amount of a lubricant in the production process for a magnetic recording medium.

On the other hand, in a magnetic recording apparatus, typically a hard disk, mainly including a recording/reproducing magnetic head and a magnetic recording medium, a friction force occurs between the magnetic head and the magnetic recording medium, thereby causing wear of the magnetic head and the magnetic recording medium. If the wear reaches a magnetic layer of the magnetic recording medium, there occurs a so-called head crush phenomenon in which information recorded in the recording layer is crushed, and accordingly, to ensure the reliability of the magnetic recording apparatus, it is important to prevent the above-mentioned head crush phenomenon.

To prevent the head crush phenomenon, it is required to improve the wear resistance of a magnetic recording medium itself. In general, to achieve such a purpose, a magnetic layer is covered with a protective layer made from carbon, an oxide, a carbide, or a nitride and further a lubricating film is formed on the protective layer. The lubricating film generally requires characteristics such as a low surface energy, heat resistance, chemical stability and lubricity. At present, a perfluoroalkylpolyether or a perfluoroalkyl compound disclosed in U.S. Pat. No. 3,778,308 has been most extensively used as a compound for forming the lubricating film.

In a magnetic recording apparatus having been mainly used at present, recording/reproducing is performed in a state in which a specific gap is kept between a magnetic head and the surface of a magnetic recording medium. Such a specific gap is called a floating amount. To enhance the recording density to the magnetic recording medium, it is required to make small the floating amount of the magnetic head. In recent years, as the recording density of a magnetic recording apparatus becomes significantly higher, the floating amount becomes smaller. Further, as the ultimate recording method, in recent years, there has been proposed a so-called contact recording method in which recording/reproducing is performed with the floating amount set to zero, that is, in a state in which a magnetic head is usually in contact with the surface of a magnetic recording medium.

In this way, as the floating amount of a magnetic head becomes smaller, a period of time in which the magnetic head is slid in contact with the surface of a magnetic recording medium becomes necessarily larger, and therefore, it is required to reduce the dynamic friction coefficient and wear by enhancing the continuously sliding durability of a lubricating film. Further, in a magnetic recording apparatus.operated in accordance with the extremely low floating method or contact recording method, since the surface roughness and waviness of a magnetic recording medium becomes smaller, a higher maximum static friction force (adhesion) is easy to occur between the magnetic head and the magnetic recording medium. The adhesion may cause the impossible starting of the magnetic recording medium or damage of the magnetic head.

The thickness of a lubricating film present on the surface of the magnetic recording medium is one major cause of occurrence of adhesion. The amount of the lubricant present on the magnetic recording medium is quantitatively measured, for example, by using an ellipsometer or in accordance with XPS (X-ray photoelectron spectroscopy). In the case of the method using the ellipsometer, since the measured result is largely affected by the surface roughness of the magnetic recording medium, it is difficult to accurately measure the amount of the lubricant. In the case of XPS, since the measurement is performed in vacuum, the lubricant on the surface of the magnetic recording medium is lost, and since the measurement is performed by using fluorine atoms, it is impossible to suitably measure a hydrocarbon based lubricant.

With respect to an optical disk (phase change type or magneto-optical type), a spacing between a conventional disk and the optical head is in a range of several hundred nm to several μm, which spacing is considerably larger than the spacing adopted for other magnetic recording methods. Accordingly, a protective film having about several hundred μm is formed on a recording layer of the optical disk. In this way, since the conventional optical disk has a large spacing, a protective film having a large thickness can be formed on the recording layer, with a result that there is a sufficient margin to take a tribological characteristic into account.

In the case of optical recording performed in a near field, which is being studied and developed at present, however, a spacing between a recording layer and an optical head may be considered to be 100 μm or less, and therefore, the thickness of a protective layer must be several ten nm or less. In this case, the tribological characteristic required for optical recording in the near field is little different from that required for the existing magnetic disk or the like. It may be considered that the surface of the optical disk be coated with an organic thin film as a lubricant layer to about several nm. Accordingly, even for the optical disk, it is required to examine the amount and orientation of a lubricating film on the optical disk just as the magnetic disk or the like.

As described above, the qualitative analysis and quantitative analysis of a lubricant on or in a medium have been based on element analysis such as XPS; however, since the element analysis is generally performed in vacuum, there is a possibility that the lubricant is evaporated. Further, since carbon atoms and hydrogen atoms are usually present as contaminants on the surface of the medium, they cannot be discriminated from the lubricant. Accordingly, only in the case where fluorine atoms are contained in the lubricant, the amount of the lubricant can be measured on the basis of the amount of fluorine atoms.

In general, not only perfluoropolyether or a perfluoroalkyl compound containing fluorine atoms but also hydrocarbon based fatty acid or fatty acid ester is used as a lubricant compound. Accordingly, the above method cannot be applied to analysis of all of the lubricant compounds. Further, in a high sensitivity reflected infrared absorption spectroscopy, since absorption of a non-magnetic supporting body cannot be sufficiently removed, the spectrum of the non-magnetic supporting body is superimposed to the spectrum of a lubricant adhering thereon, with a result that it is very difficult to discriminate only the spectrum of the lubricant.

SUMMARY OF THE INVENTION

An object of the present invention is to provide an optical analysis apparatus, more specifically, an infrared microscopic/FT-IR apparatus capable of simply, accurately performing qualitative analysis and quantitative analysis of an organic thin film on a high density recording medium and an organic material in the medium, and an analysis method for the high density recording medium using the apparatus.

According to a first aspect of the present invention, there is provided an infrared microscopic/FT-IR (Fourier transform infrared spectrometer) apparatus based on an attenuated total reflection method, the apparatus including: a semi-spherical prism having a smooth, flat bottom surface; and an incident angle variable optical system in which a sample mounting portion is separated from an incident optical system by the semi-spherical prism; whereby a surface portion of a sample is analyzed by bringing the prism in press-contact with the surface of the sample, making an infrared light ray incident on the prism at a specific angle, and analyzing the spectrum of the infrared light ray totally reflected from the surface of the sample by the FT-IR apparatus.

The above incident angle variable optical system may be housed in an enclosed sample chamber.

The above incident angle variable optical system may include parabolic mirrors opposed to each other.

The above apparatus may further includes a contact pressure control means for finely adjusting a contact pressure applied from the surface of the sample to the bottom surface of the semi-spherical prism.

According to a second aspect of the present invention, there is provided an infrared microscopic/FT-IR apparatus based on an attenuated total reflection method, the apparatus including: a semi-spherical prism having a smooth, flat bottom surface; and a contact pressure control means for finely adjusting a contact pressure applied from the surface of the sample to the bottom surface of the semi-spherical prism; whereby a surface portion of a sample is analyzed by bringing the prism in press-contact with the surface of the sample, making an infrared light ray incident on the prism at a specific angle, and analyzing the spectrum of the infrared light ray totally reflected from the surface of the sample by the FT-IR apparatus.

According to a third aspect of the present invention, there is provided a method for carrying out at least one of qualitative analysis and quantitative analysis for a surface portion of a recording medium, including the steps of: preparing an infrared microscopic/FT-IR apparatus based on an attenuated total reflection method, the apparatus including a semi-spherical prism having a smooth, flat bottom surface, and an incident angle variable optical system in which a sample mounting portion is separated from an incident optical system by the semi-spherical prism; bringing the prism in press-contact with the surface of the sample; making an infrared light ray incident on the prism at a specific angle; and analyzing the spectrum of the infrared light ray totally reflected from the surface of the sample by the FT-IR apparatus.

According to a fourth aspect of the present invention, there is provided a method for carrying out at least one of qualitative analysis and quantitative analysis for a surface portion of a recording medium, including the steps of: preparing an infrared microscopic/FT-IR apparatus based on an attenuated total reflection method, the apparatus including a semi-spherical prism having a smooth, flat bottom surface, and a contact pressure control means for finely adjusting a contact pressure applied from the surface of the sample to the bottom surface of the semi-spherical prism; bringing the prism in press-contact with the surface of the sample; making an infrared light ray incident on the prism at a specific angle; and analyzing the spectrum of the infrared light ray totally reflected from the surface of the sample by the FT-IR apparatus.

In the above method, the recording medium may be a coating type magnetic recording medium in which a magnetic layer is formed on a non-magnetic supporting body by a coating film mainly containing a ferromagnetic powder and a binder and additionally containing an organic lubricant.

In the above method, preferably, the recording medium may be a metal thin film type magnetic recording medium in which a metal thin is formed on a non-magnetic supporting body and a magnetic layer containing an organic lubricant is formed on the metal thin film.

In the above method, the recording medium may be a metal thin film optical recording medium in which an optical recording layer is formed on a non-magnetic supporting body and an organic thin film containing an organic lubricant is formed on the surface of the optical recording layer.

In the above method, an infrared light ray having a wavelength ranging from 2 µm to 20 µm may be made incident on the prism.

In the above method, the semi-spherical prism may have a refractive-index ranging from 2.0 to 4.0.

According to the analysis method of the present invention, the contact pressure applied from the surface of a sample during analysis to the bottom surface of the semi-spherical prism by the contact pressure control means is preferably in a range of 10 kgf/cm$^2$ or less.

The reason why an infrared light ray is made incident on the prism in the state in which the contact pressure is kept at a value in the range 10 kgf/cm$^2$ or less is for uniformly keeping the press-contact state between the surface of a sample and the bottom surface of the prism over the entire contact area, thereby performing high accurate analysis of the sample at a desired surface position and also obtaining an analysis result with a good repeatability. Additionally, in the case where a recording medium such as a floppy disk, a magnetic tape, a magnetic disk or an optical disk is taken as a sample, if the contact pressure is selected to be more than 10 kgf/cm$^2$, the sample may be broken and thereby it is impossible to analyze the sample.

The above contact pressure control means preferably includes a presser metal, a pressing mechanism for bringing the presser metal into press-contact with the surface of a sample, a pressure detecting mechanism for detecting the contact pressure between the surface of the sample and the bottom surface of the prism, and a control mechanism for controlling the contact pressure in a specific range by suitably moving the presser metal by means of the pressing mechanism on the basis of detection data obtained by the pressure detecting mechanism. To be more specific, the presser metal is brought into press-contact with the surface of the sample by a spring or a hydraulic mechanism; the contact pressure is detected by a sensor such as a piezoelectric element connected to the control mechanism; and if the contact pressure is out of the above specific range, the presser metal is suitably moved by operating the pressing mechanism on the basis of a signal supplied from the control mechanism.

Examples of high density recording media capable of being analyzed according to the present invention may include (1) a coating type magnetic recording medium in which a magnetic paint mainly containing a binder and a ferromagnetic powder and additionally containing an organic lubricant is applied on a non-magnetic supporting body to form a magnetic layer; (2) a metal thin film type magnetic recording medium in which a metal thin film is formed on a non-magnetic supporting body and a magnetic layer containing an organic lubricant is formed on the metal thin film; and (3) a metal thin film type optical recording medium in which an optical recording layer is formed on a non-magnetic supporting body and an organic thin film containing an organic lubricant is formed on the surface of the optical recording layer.

Concretely, a magnetic tape (audio tape or video tape), a floppy disk, an optical disk (magneto-optical type or phase change type), and a hard disk are taken as the above high density recording media.

That is to say, according to the present invention, it is possible to simply, accurately perform at least one of qualitative analysis and quantitative analysis of an organic material, particularly an organic lubricant in or on the above high density recording medium. The lubricant on the recording medium means a lubricant present on the uppermost surface, opposed to the supporting body, of the recording medium, while the lubricant in the recording medium means a lubricant contained in the recording medium, that is, present in a layer between the surface of the supporting body and the uppermost surface of the recording medium. It should be noted that in the following description, the organic lubricant and the recording medium are sometimes referred to simply as "lubricant" and "medium", respectively.

In the analysis method of a high density recording medium according to the present invention, the surface of a sample is brought into press-contact with the bottom surface (smooth plane) of the semi-spherical prism at a specific contact pressure; an infrared light ray having a wavelength ranging from 1 µm to 20 µm is made incident on the spherical plane of the semi-spherical prism (hereinafter, sometimes referred to simply as a "prism"); the spectrum of an organic matter in the uppermost surface layer portion (depth: 100 nm to several nm) of the sample is obtained by an evanescent wave leaked from inner reflection in the prism; and the spectrum is analyzed by using a Fourier transformer. The prism is made from a crystal which is transparent for infrared light rays and has a refractive index being as high as possible, for example, a crystal of germanium (Ge) or silicon (Si).

In the ordinary high sensitivity reflected infrared absorption spectroscopy, unless the reflectance of the surface of the sample is very high, light incident from a light source is absorbed in a sample, thereby making it impossible to attain satisfactory measurement. For a metal thin film type magnetic recording medium, a coating type magnetic recording medium, and an optical recording medium, since the reflectance of the surface of the medium is low, it is impossible to analyze a trace of lubricant on and in the medium by the high sensitivity reflected infrared spectroscopy.

To be more specific, in the high sensitivity reflected infrared absorption spectroscopy, analysis is performed by making a light ray incident on the surface of a sample at an angle of about 80° with respect to the normal line of the surface of the sample, and allowing the light ray to be reflected from the surface of the sample at one time. Such a spectroscopy is generally suitable for analysis of an organic matter on the surface of a metal underlying film having a high reflectance, and is effective for analysis of an organic matter on a hard disk. However, since the reflectance of a recording medium such as a magnetic tape or a floppy disk is generally very low, it is impossible to analyze an organic matter on and in the recording medium. On the contrary, it is possible to accurately analyze an organic matter on and in any sample irrespective of the reflectance of the sample.

In an ATR method (attenuated reflection method utilizing multi-reflection) based on a general internally reflected infrared absorption spectroscopy, samples are overlapped on upper and lower surfaces of a plate-like prism; a packing and fastening plate are overlapped on the back surface of each sample; the samples and the prism are fastened with a bolt and a nut; and the samples thus assembled to the prism are set in a measuring apparatus for analysis. In this method, since fine adjustment is required to uniformly keep the press-contact state between the plate-like prism and the surface of the sample over the contact area, it is very difficult to perform accurate analysis. Further, if the amount of an object to be measured differs depending on the position on the surface of the sample, only an average value of the amounts of the object in a wide range on the sample can be obtained. In the case of adopting the ATR method, the concentration distribution of a lubricant at a micro-region (having a radius of 1 mm or less) cannot be obtained, unlike the present invention.

On the contrary, according to the analysis method of the present invention, since the semi-spherical prism is used and the contact pressure between the surface of a sample and the bottom surface of the prism is set in a specific range, the press-contact state can be uniformly kept in a wide range, with a result that an infrared light ray made incident on the prism can be simply, certainly converged at a specific position on the surface of the sample. As a result, it is possible to accurately perform qualitative analysis and quantitative analysis of a trace of lubricant present on and in the medium and to obtain the concentration of the lubricant at a micro-region (having a radius of 1 mm or less) at a very high sensitivity (that is, high S/N ratio).

From the examination performed by the present inventors, it is confirmed that in the case of analyzing a lubricant on and in a recording medium according to the present invention, to perform accurate analysis with a good repeatability, a difference in contact pressure applied from the surface of a sample to the bottom surface of the prism between two of the analysis operations is required to be in a range of several ten $mgf/cm^2$ or less, and it can be controlled in a range of several $mgf/cm^2$ or less by the contact pressure control means.

In the analysis method of the present invention, an infrared light ray having a wavelength ranging from 2 $\mu$m to 20 $\mu$m is used. The reason for this is that organic materials have absorption characteristics over a wide infrared light range, and most of organic materials absorb an infrared light ray having a wavelength ranging from 2 $\mu$m to 20 $\mu$m.

To accurately analyze a sample in a depth range from the uppermost surface to 1–2 $\mu$m, the refractive index of the semi-spherical prism may be in a range of 1.5 to 5.0, preferably, 2.0 to 4.5. According to the present invention, the use of the prism having a larger refractive index is effective to analyze the uppermost surface of a sample, and the use of the prism having a smaller refractive index make it difficult to analyze the uppermost surface of the sample because of permeation of an infrared light ray to a deeper point in the sample.

To be more specific, according to the analysis method of the present invention, when a light ray is totally reflected at the interface between the prism and the surface of a sample, an evanescent wave occurs from the surface of the prism and permeates in the surface of the sample, with a result that information only from the uppermost surface of the sample can be obtained. If the refractive index of the prism is small (for example, 0.2), the above permeation depth becomes several $\mu$m or more, therefore it is difficult to analyze the uppermost surface of the sample or its directly underlying portion (equivalent to a magnetic layer of a magnetic recording medium). The prism having a refractive index ranging from 2.0 to 4.5 is readily available and is effective to accurately analyze the uppermost surface of the sample and its directly underlying portion. The prism which is transparent for infrared light rays and has a refractive index of more than 4.5 is not readily available.

The present invention can be configured such that not only a lubricant on the uppermost surface of a medium but also an organic material in the medium can be analyzed. The reason for this is that an organic material, particularly a lubricant in the recording medium exerts a large effect on the reliability of the medium, and even for the same total amount of the lubricant on and in the medium, the reliability of the medium largely differs depending on the existing state of the lubricant in the medium (concentration distribution in the depth direction and the concentration on the surface). The accurate analysis of an organic material in a medium, which has been not achieved by the related art method, can be achieved by the present invention, and therefore, the present invention has an extremely important technical significance.

Since the incident angle variable optical system of the present invention is separated from the sample mounting portion by means of the semi-spherical prism, only the optical system can be enclosed, to facilitate the operation such as exchange of a sample. Also, since the optical system is enclosed, it is possible to prevent, upon exchange of a sample, the permeation of carbon dioxide or moisture in the optical path of the optical system and hence to suppress noise due to carbon dioxide or moisture, and also to eliminate the necessity of taking an excessive waiting time for substituting, after exchange of the sample, the interior of a sample chamber for nitrogen gas or the like for removing carbon dioxide or moisture.

BRIEF DESCRIPTION OF THE DRAWINGS

FIG. 12 is a graph showing the analysis results obtained in Inventive Examples 1 to 4;

DETAILED DESCRIPTION OF THE PREFERRED EMBODIMENT

First Embodiment

Figure 1:
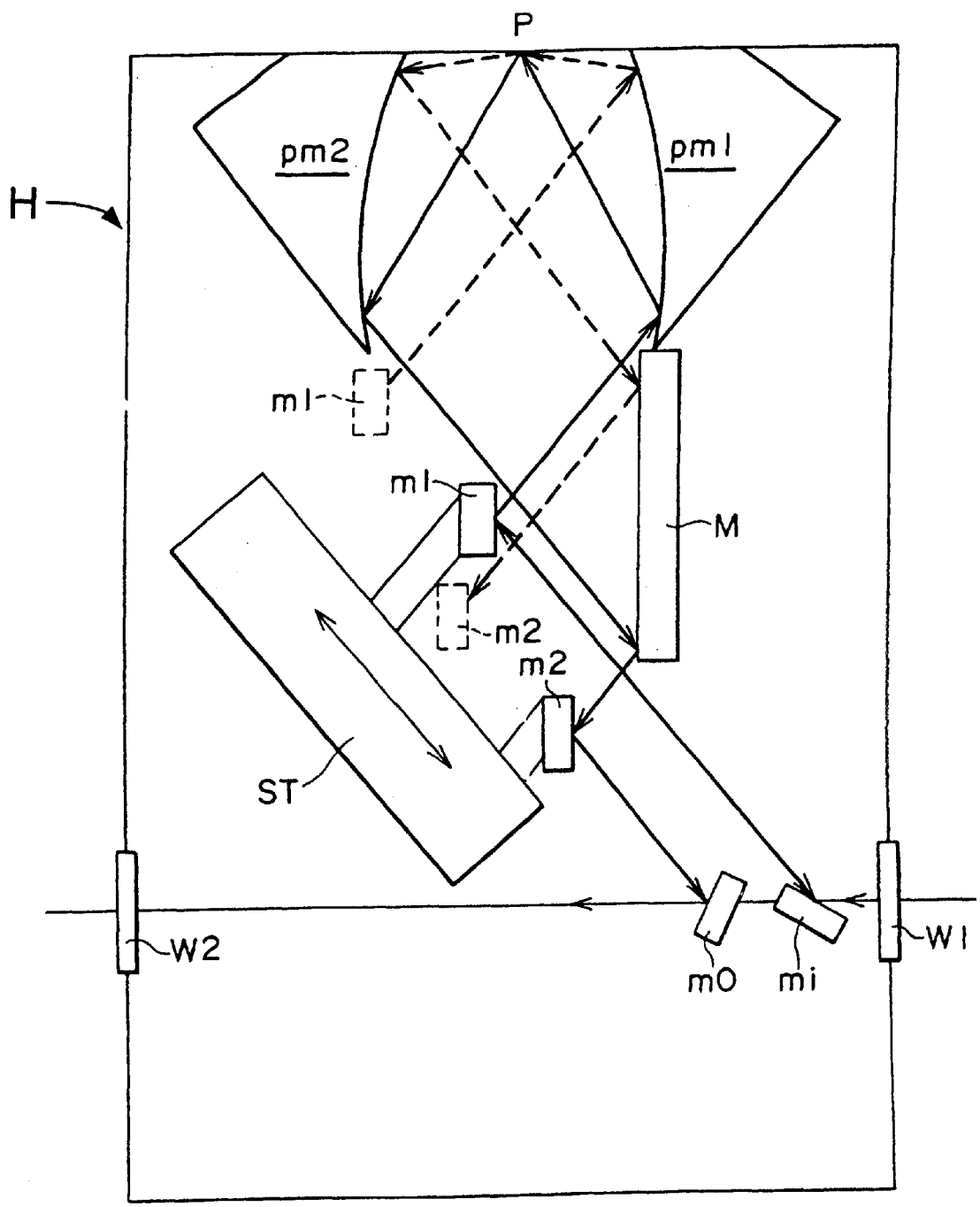
FIG. 1 is an illustrative diagram of an optical system of an infrared microscopic/FT-IR apparatus of the present invention.

An optical system of an infrared microscopic/FT-IR apparatus according to the present invention will be first described with reference to FIG. 1. The optical system is housed in an enclosed sample chamber, that is, a case H. Characters pm1 and pm2 designate parabolic mirrors opposed to each other, and P designates a focal point thereof. A semi-spherical prism (not shown) is disposed at the focal point, and a sample is mounted on the prism. Characters mi and mo designate an incoming light reflecting mirror and an outgoing light reflecting mirror, respectively; and m1 and m2 designate movable mirrors for controlling the incident angle of light. The movable mirror m1 and m2 are mounted on a common movable stage ST in such a manner as to be translatable integrally with the movable stage ST. Character M designates a return mirror; and W1 and W2 designate an incoming light passing window and an outgoing light passing window, respectively. Additionally, the above case H is provided with an opening/closing port and an opening/closing lid (not shown) for exchange of a sample, which are located at a position over a gap between the opposed parabolic mirrors pm1 and pm2.

The function of the above optical system will be described below. An infrared light ray having entered in the case H through the incoming light passing window W1 is reflected from the incoming light reflecting mirror mi to be led to the movable mirror m1. The movable mirror m1 is movable in parallel to the optical path by movement of the movable stage ST, so that the incident position of light on the parabolic mirror pm1 is variable with the optical path kept in parallel. Light rays incident on the parabolic mirror pm1 in parallel to the optical axis are all incident on the focal point P. At this time, the incident angle of light on the focal point P varies (in FIG. 1, the optical path shown by the solid line varies into the optical path shown by the dotted line) by movement of the incident position of light on the parabolic mirror pm1 (in FIG. 1, the mirrors m1 and m2 shown by the solid line are moved to the mirrors m1 and m2 shown by the dotted line). The light ray reflected from the focal point P is led to the opposed parabolic mirror pm2 in a state in which the incident angle of the light rays having been incident from the parabolic mirror pm1 on the focal point P remains unchanged. The light ray emerged from the parabolic mirror pm2 is returned by the return mirror M to be led to the movable mirror m2 in parallel to the incident light ray having been incident on the parabolic mirror pm1. In this way, the incident angle of light on the focal point P (which is the mounting position of the semi-spherical prism) is made variable by translating the movable mirror m1 and m2 by means of movement of the movable stage ST.

Additionally, the configuration in which the incident angle variable optical system is housed in the enclosed case H (sample chamber) is advantageous in that, upon exchange of a sample at the position over the focal point P, permeation of outside air in the optical system can be prevented; and the exchange of a sample can be easily performed.

Figure 2:
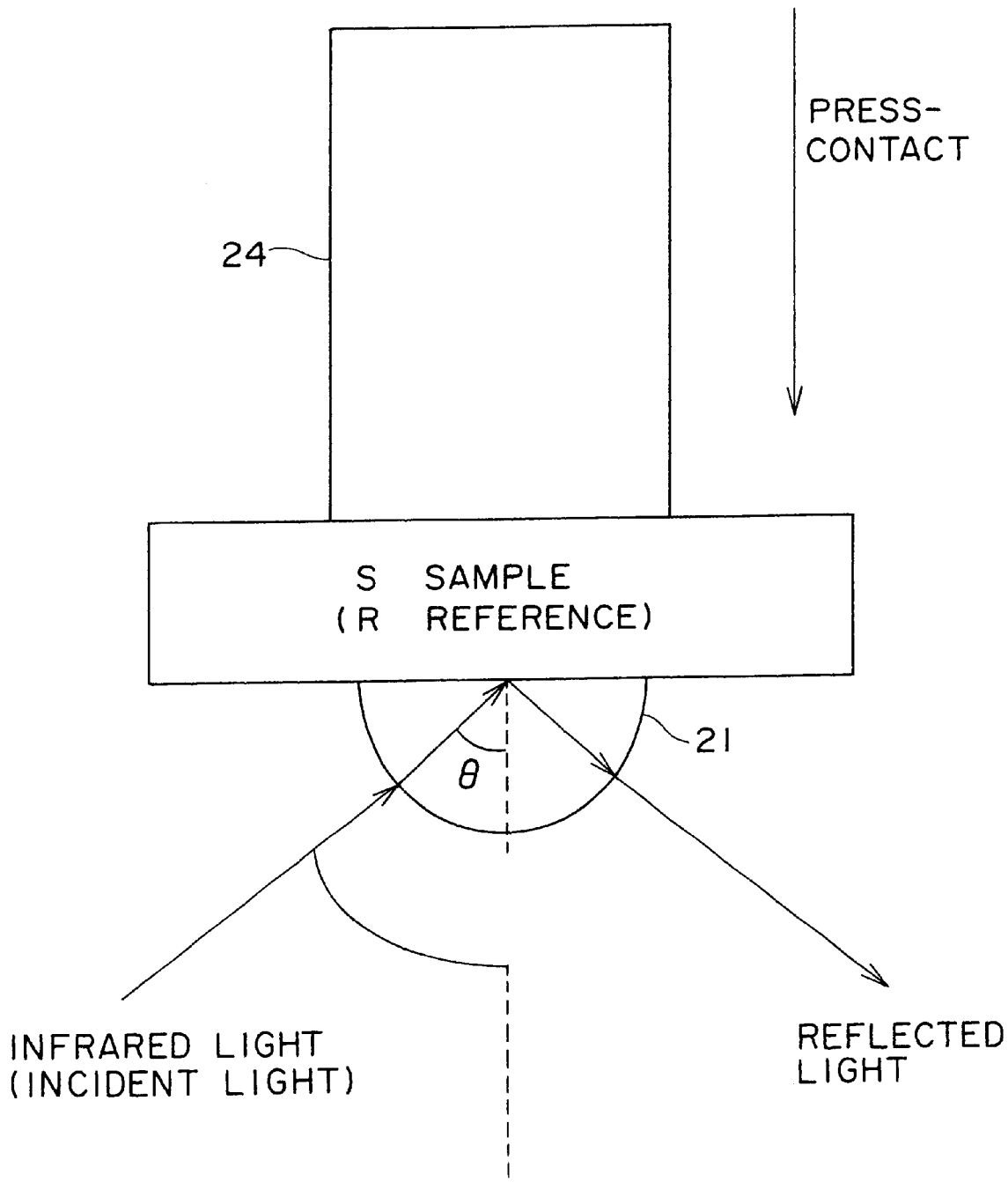
FIG. 2 is an illustrative view of the configuration of an essential portion of the infrared microscopic/FT-IR apparatus of the present invention.
Figure 3:
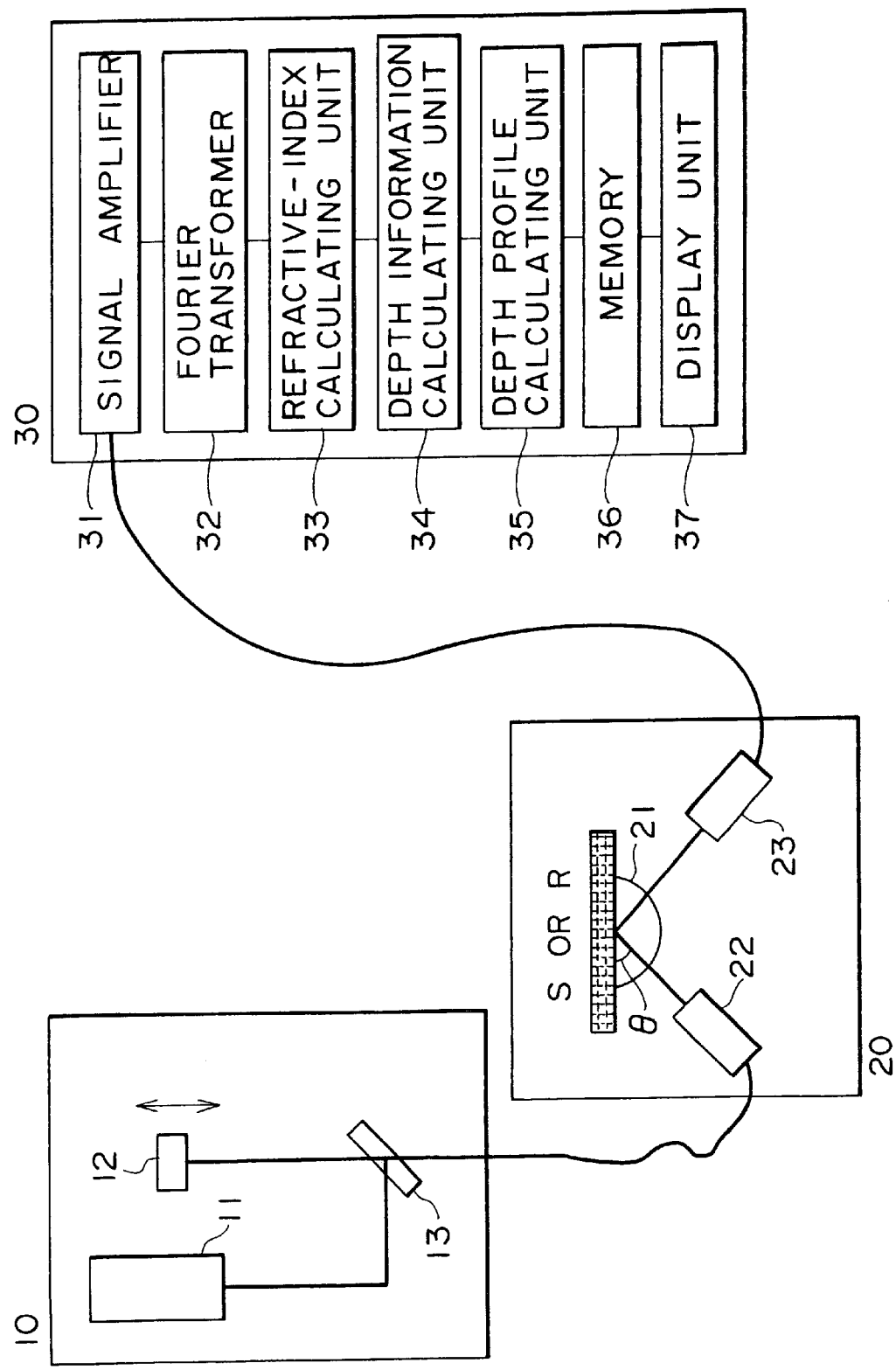
FIG. 3 is an illustrative diagram of the configuration of a single beam measuring apparatus.
Figure 4:
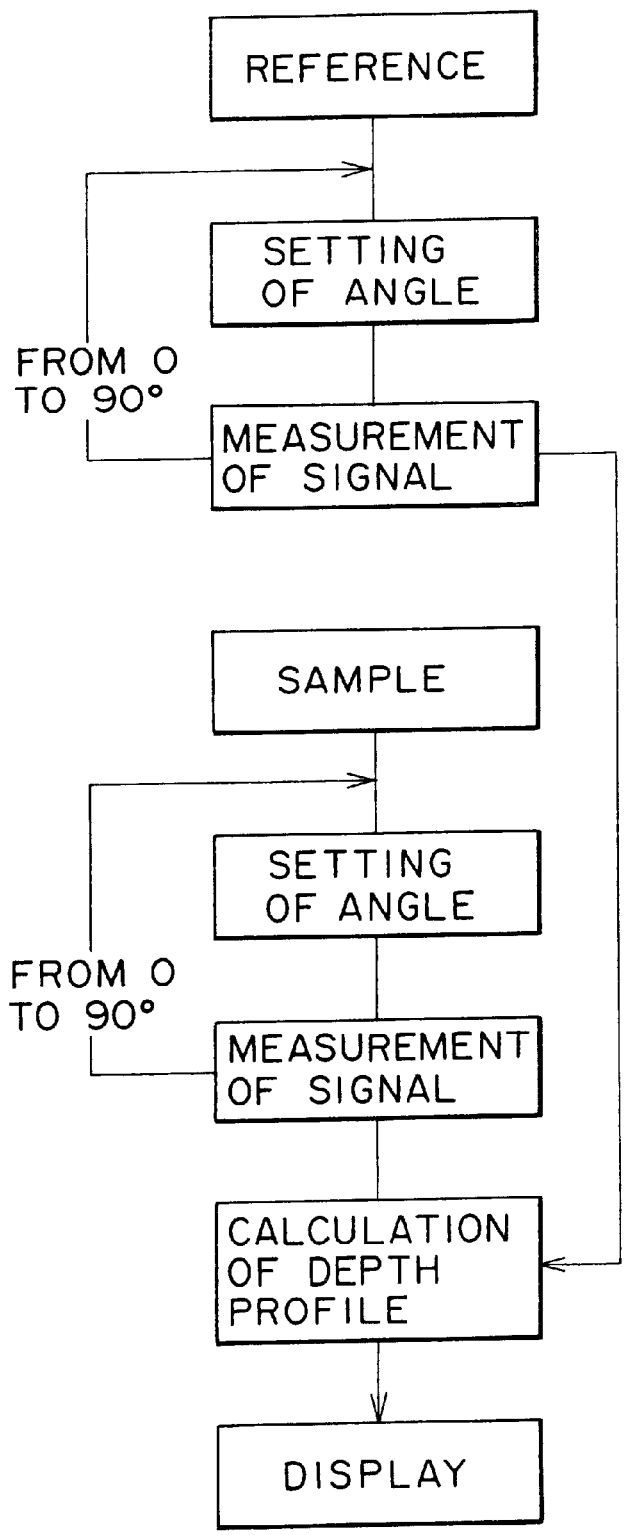
FIG. 4 is a flow chart showing an analysis method using the measuring apparatus shown in FIG. 3.

Hereinafter, the embodiment in which the present invention is applied to a floppy disk will be described with reference to the drawings. FIG. 2 is a typical sectional view showing the configuration of an essential portion of the infrared microscopic/FT-IR apparatus; FIG. 3 is a diagram illustrating the configuration of a single beam measuring apparatus; and FIG. 4 is a flow chart showing a method for analysis using an analysis apparatus shown in FIG. 3.

A single beam measuring apparatus is composed of an interference light source unit 10, a measuring unit 20, and a signal processing unit 30. An infrared light source 11, a movable mirror 12, and a half mirror 13 are provided in the interference light source unit 10. The measuring unit 20 is configured such that a semi-spherical prism 21, an incident angle varying device 22, and a detector 23 are provided in a sample chamber (not shown). A signal amplifier 31, a Fourier transformer 32, a refractive-index calculating unit 33, a depth information calculating unit 34, a depth profile calculating unit 35, a memory 36, and a display unit 37, which are connected to each other in this order, are provided in the signal processing unit 30.

In the above sample chamber, as shown in FIG. 2, a floppy disk used as a reference R is set on the bottom of semi-spherical prism 21 made from germanium or silicon in such a manner that a plane to be analyzed of the reference R, that is, a plane on the magnetic layer formation side of a supporting body of the floppy disk is brought in press-contact with the bottom surface of the semi-spherical prism 21 at a suitable pressure of 10 kgf/cm$^2$ or less by using a contact pressure control unit 24. Then, the reference R is subjected to analysis in accordance with the flow chart shown in FIG. 4. Next, in place of the reference R, a sample S is set in the sample chamber in the same manner as described above, and is subjected to the same analysis.

In this case, to enhance the analytical accuracy, it is important to adjust a contact pressure Ps applied from the sample S to the prism 21 to be identical or substantially identical to a contact pressure Rs applied from the reference R to the prism 21. It should be noted that the reference R is different from the sample S in that any magnetic layer is not provided in the reference R. Hereinafter, the procedure of the above analysis will be described in detail.

The refractive-index of the semi-spherical prism 21 is previously measured by a suitable means. Then, the refractive-index of the plane to be analyzed of each of the reference R and the sample S is measured. For example, the refractive-index of the plane to be analyzed of the sample S is measured in the following procedure. The sample S is set on the measuring unit 20 shown in FIG. 3 in the manner shown in FIG. 2. An infrared light ray (wave number, for example, ranging from 400 cm$^{-1}$ to 5000 cm$^{-1}$) emitted from the infrared light source 11 is made incident on the semi-spherical prism 21. At this time, the incident angle θ (see FIG. 2) of the infrared light ray incident on the semi-spherical prism 21 is scanned in a suitable range (for example 30° to 80°) narrower than the range of 0° to 90° by the incident angle varying device 22. During this scanning period, the infrared absorbance of the sample S against the incident angle θ is plotted by the information signal unit 30. The refractive-index of the sample S is thus automatically calculated by the refractive-index calculating unit 33 on the basis of both the incident angle at the time when the absorbance is minimized (that is, when light ray is total-reflected) and the refractive-index of the prism.

Next, an organic material in a surface layer of the sample S is subjected to qualitative analysis and quantitative analysis in accordance with the flow chart shown in FIG. 4 by using the analysis apparatus shown in FIG. 3. In accordance with the same manner as described above, an incident angle θ of the infrared light ray incident from the infrared light source 11 on the semi-spherical prism 21 is scanned in a suitable range narrower than the range of 0° to 90° by the incident angle varying device 22. During this scanning period, the reflected light ray from the sample S is processed by the signal amplifier 31 and the Fourier transformer 32, to thereby automatically calculate a depth profile in the following manner by the refractive-index calculating unit 33 while obtaining an infrared absorption spectrum.

To be more specific, a permeation depth "d" (usually, ranging from 100 nm to several μm) of an evanescent wave of the infrared light ray at each incident angle from the surface of the sample S is calculated in accordance with the following equation by using the wavelength λ of the infrared light ray, the incident angle θ, a refractive index np of the semi-spherical prism 21 and a refractive-index ns of the sample S which are previously measured.

$$d = \lambda / [2\pi np \cdot \{\sin^2\theta - (ns/np)^2\}^{1/2}] \quad (1)$$

where π is the ratio of the circumference of a circle to its diameter, and ns/np is the ratio of ns to np, which ratio is less than 1.

Figure 7:
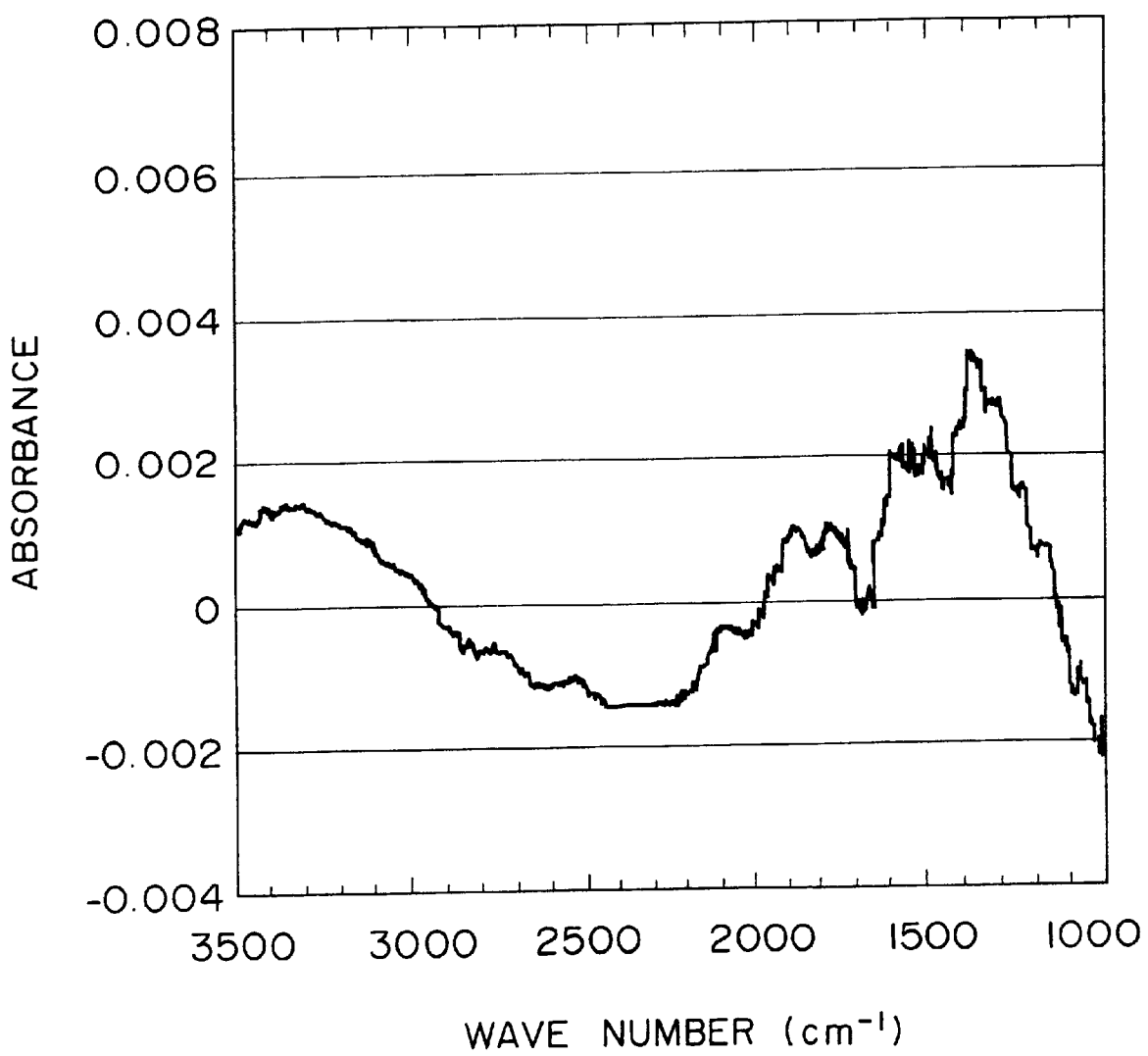
FIG. 7 is an infrared absorption spectrum obtained in Inventive Example 1 of the present invention.
Figure 8:
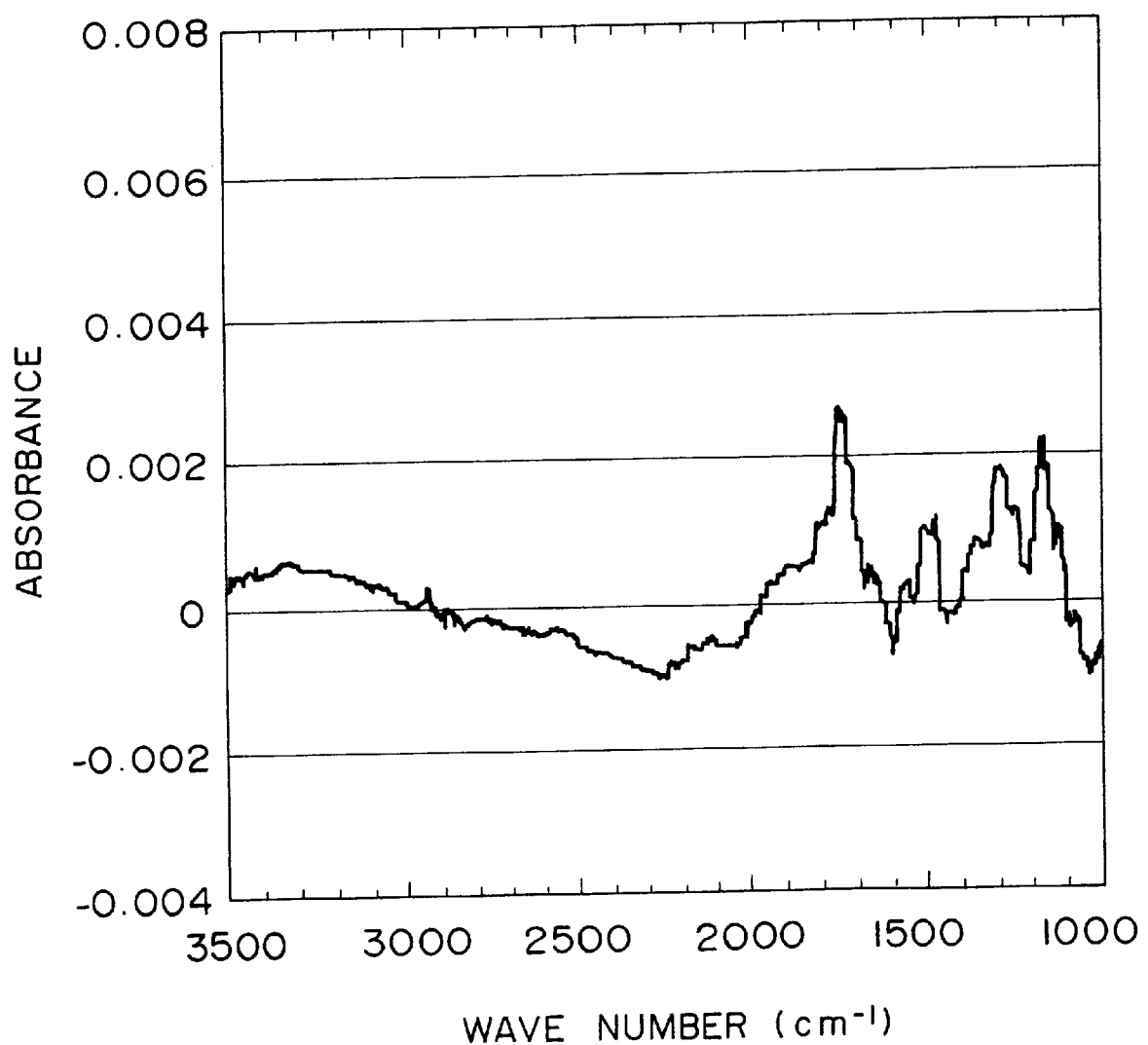
FIG. 8 is an infrared absorption spectrum obtained in Inventive Example 2 of the present invention.
Figure 9:
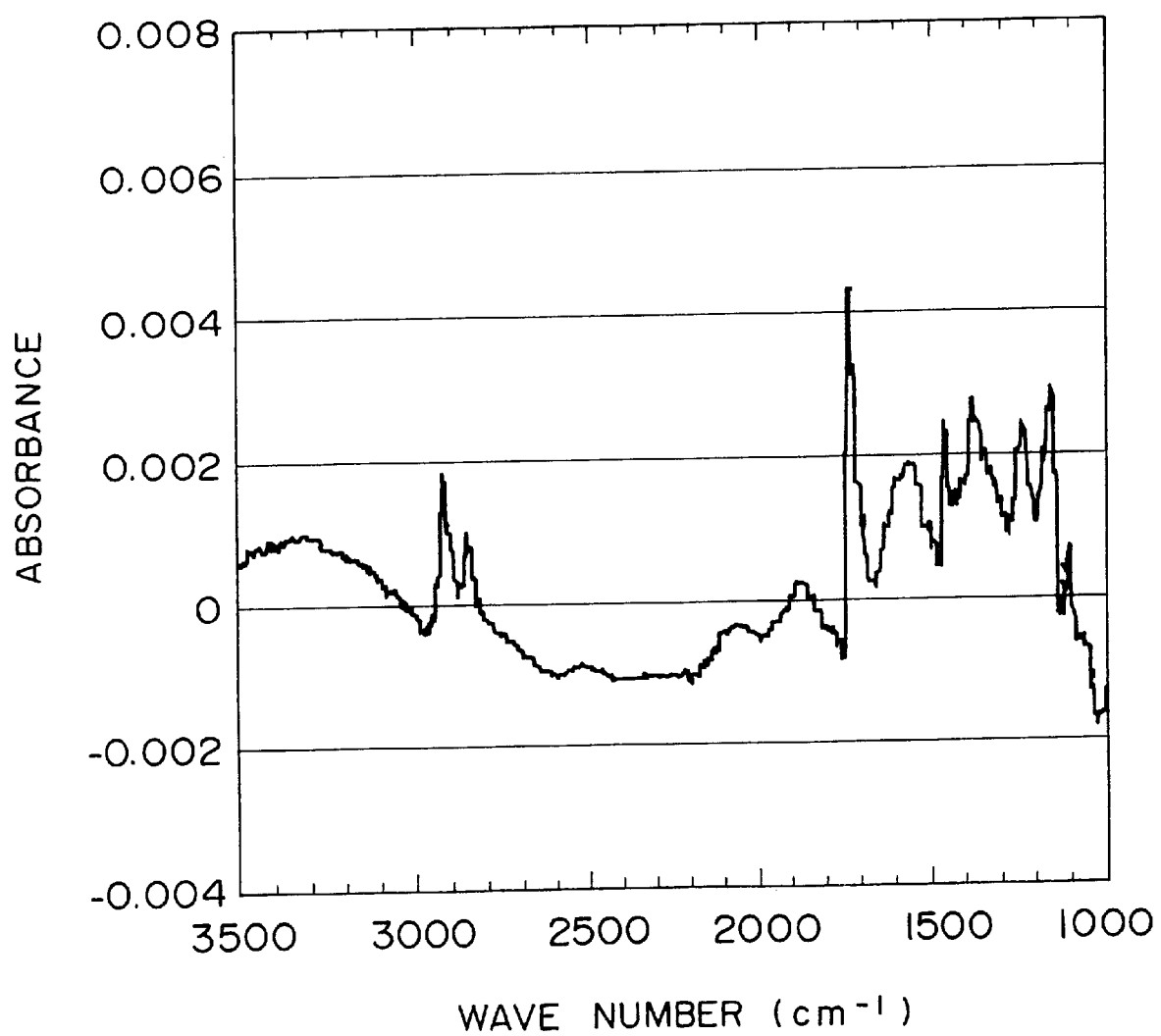
FIG. 9 is an infrared absorption spectrum obtained in Inventive Example 3 of the present invention.
Figure 10:
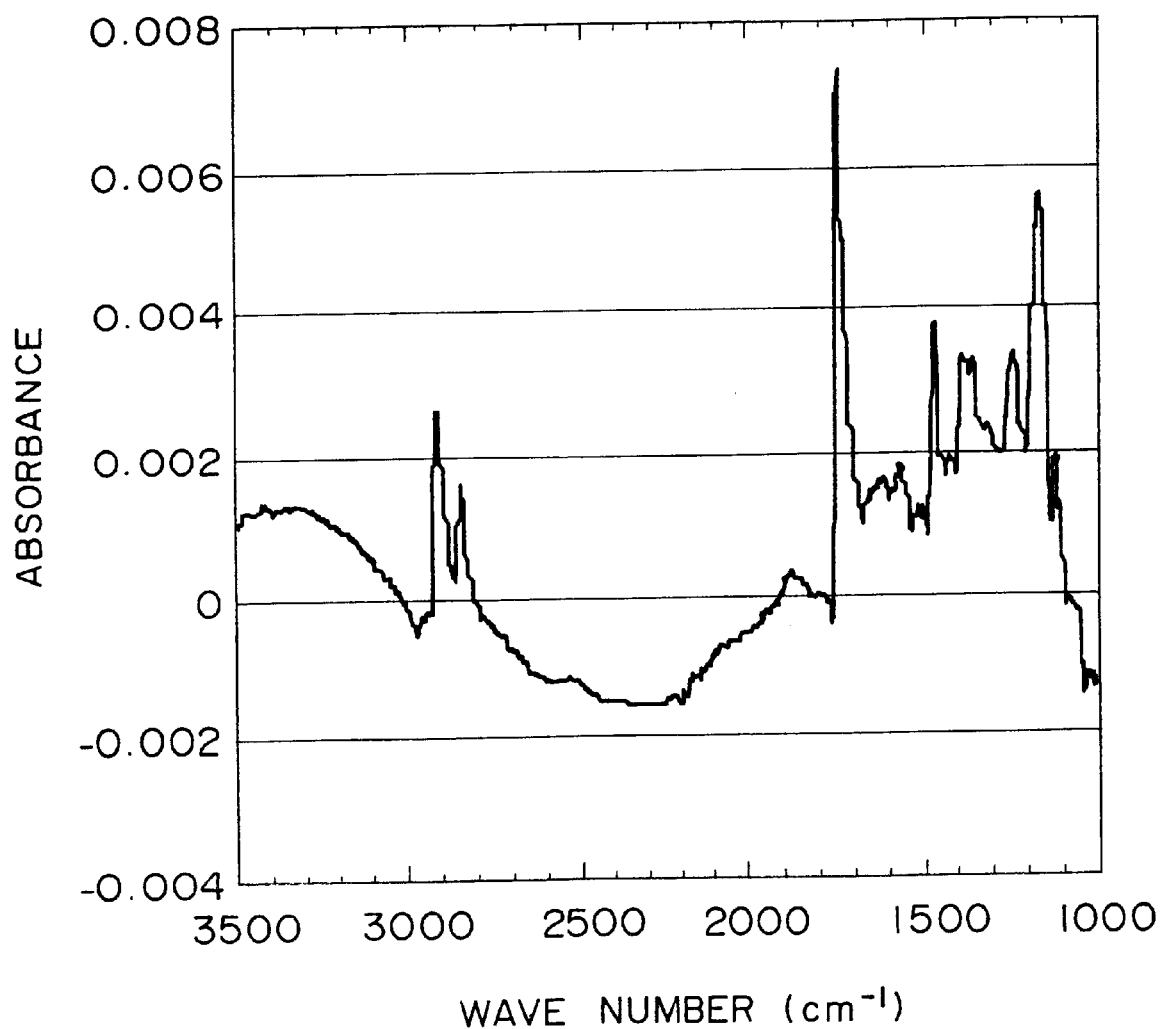
FIG. 10 is an infrared absorption spectrum obtained in Inventive Example 4 of the present invention.

On the basis of the permeation depth "d" and the absorbance of the infrared absorption spectrum (see FIG. 7 to be described later), the above depth profile, that is, the concentration distribution of the organic material in the depth direction of the sample S is quantitatively calculated by the depth information calculating unit 34 and the depth profile calculating unit 35, and the result is recorded in the memory 36 and is displayed on the display unit 37. The qualitative analysis for the organic material is performed by analyzing the resultant infrared absorption spectrum in accordance with the usual manner. The same procedure is performed for the reference R. Finally, the quantitative analysis and the qualitative analysis for the sample S are performed by comparing the analysis result for the sample S with that for the reference R.

Second Embodiment

Figure 5:
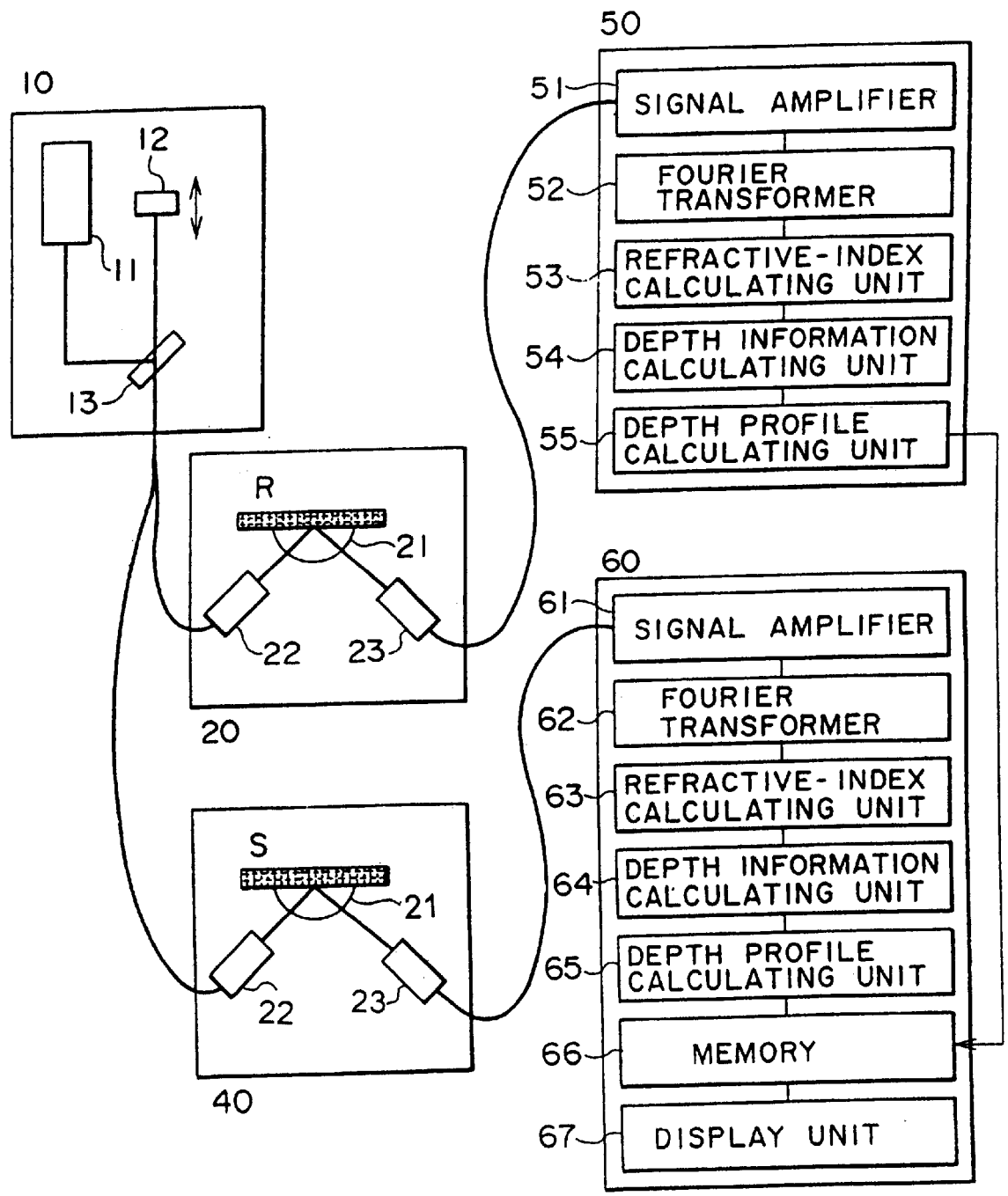
FIG. 5 is an illustrative diagram of the configuration of a double beam measuring apparatus.
Figure 6:
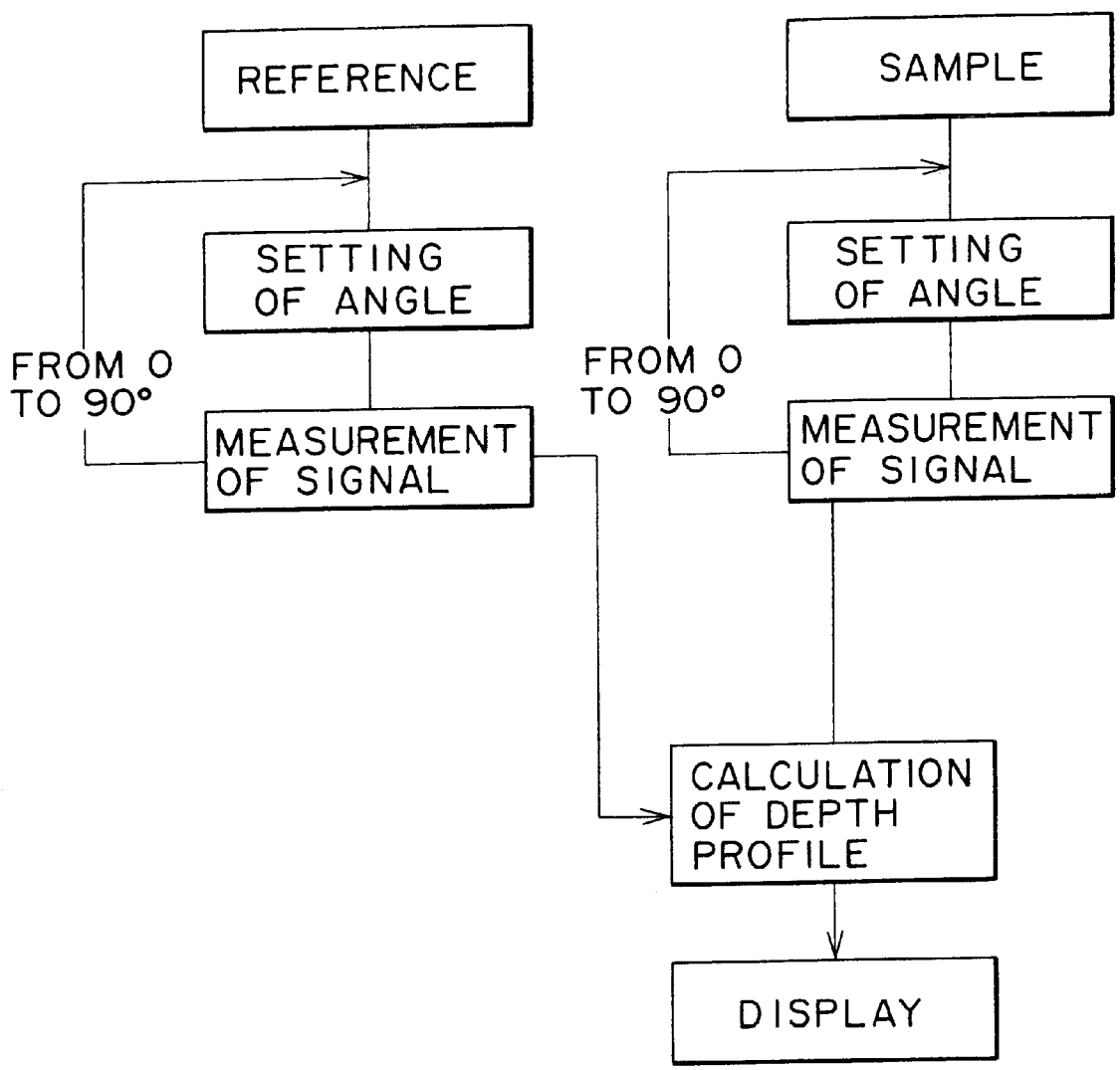
FIG. 6 is a flow chart showing an analysis method using the measuring apparatus shown in FIG. 5.

Another embodiment in which the present invention is applied to a floppy disk will be described with reference to the drawings. FIG. 5 is a diagram illustrating the configuration of an infrared microscopic/FT-IR apparatus using double beams, and FIG. 6 is a flow chart showing a method for analysis using the analysis apparatus shown in FIG. 5.

The analysis apparatus shown in FIG. 5 is composed of an interference light source unit 10, a measuring apparatus 20 for the reference R, a measuring apparatus 40 for the sample S, a signal processing unit 50, and a signal processing unit 60. The interference light source 10 has the same configuration as that of the interference light source 10 shown in FIG. 3. Each of the measuring units 20 and 40 has the same configuration as that of the measuring unit 20 shown in FIG. 3. The measuring units 20 and 40 are connected in parallel to the interference light source 10. The measuring unit 20 is connected in series to the signal processing unit 50, and the measuring unit 40 is connected in series to the signal processing unit 60.

In the signal processing unit 50, a signal amplifier 51, a Fourier transformer 52, a refractive-index calculating unit 53, a depth information calculating unit 54, and a depth profile calculating unit 55 are connected in series to each other in this order. In the signal processing unit 60, a signal amplifier 61, a Fourier transformer 62, a refractive-index calculating unit 63, a depth information calculating unit 64, a depth profile calculating unit 65, a memory 66, and a display unit 67 are connected in series in this order. The depth profile calculating unit 55 in the signal processing unit 50 is connected to the memory 66 in the signal processing unit 60.

The analysis apparatus shown in FIG. 3 is characterized in that the reference R and the sample S are analyzed by using the common (single) measuring unit 20 and the common (single) signal processing unit 30. On the other hand, the analysis apparatus shown in FIG. 5 is characterized in that (1) the reference R and the sample S are parallelly (simultaneously) subjected to detection of reflected light by providing the measuring unit 20 specialized for the reference R and the measuring unit 40 specialized for the sample S, and that (2) the reflected light from the reference R and the reflected light from the sample S are parallelly analyzed by the signal processing units 50 and 60, respectively, and the measured result of the profile of an organic material in the depth direction for each of the reference R and the sample S is recorded in the common memory 66 and displayed on the common display unit 67.

The analysis apparatus shown in FIG. 5 is superior to that shown in FIG. 3 in that the reference R and the sample S can be usually, simultaneously measured to thereby obtain highly accurate analysis results. The procedure of the method for analysis by using the analysis apparatus shown in FIG. 5 is basically the same as that in the first embodiment, and therefore, the overlapped description thereof is omitted.

The present invention will be more fully understood by way of the following examples:

Inventive Example 1

A magnetic tape as a recording medium was experimentally produced by coating the front surface of a supporting body with a magnetic paint having the following composition to form a magnetic layer, and coating the back surface of the supporting body with a back paint having the following composition to form a back coat layer.

<Composition of Magnetic Paint>

| | |
|---|---|
| Fe based ferromagnetic metal powder (coercive force = 160 kA/m, saturation magnetization amount = 145 Am²/kg, specific surface area = 51 m²/g, major axis length = 0.08 μm, acicular ratio = 3) | 100 parts by weight |
| polyvinyl chloride resin (trade name MR-110, sold by Nippon Zeon Co., Ltd.) | 14 parts by weight |
| polyester-polyurethane resin (sold by Toyobo Co., Ltd.) | 3 parts by weight |
| additive (Al₂O₃) | 5 parts by weight |
| lubricant (heptyl stearate) | 0.5 part by weight |
| solvent: | |
| (1) methyl ethyl ketone | 150 parts by weight |
| (2) cyclohexane | 150 parts by weight |

The magnetic paint was prepared by mixing the ferromagnetic powder, binder (resin), additive, lubricant, and solvent in accordance with the usual manner, kneading the mixture by an extruder, and dispersing the components of the mixture for 6 hr by a sand mill. Then, 3 parts by weight of polyisocyanate was added to 100 parts by weight of the magnetic paint, and was applied to one surface of a film of PET (polyetyleneterephthalate) having a thickness of 7 μm, to form a magnetic layer having a thickness of 6.5 μm. The magnetic layer was subjected to orientation treatment by a solenoid coil, followed by drying, calendering, and hardening treatments. Next, the back paint having the following composition was applied to the back surface of the above PET film, and cut into a width of 8 mm, to prepare a magnetic tape.

<Composition of Back Paint>

| | |
|---|---|
| carbon black #50 | 100 parts by weight |
| polyester-polyurethane resin (Nipporan N-2304) | 100 parts by weight |
| solvent: | |
| (1) methyl ethyl ketone | 500 parts by weight |
| (2) cyclohexane | 500 parts by weight |

Inventive Example 2

A magnetic tape was prepared in accordance with the same manner as that in Inventive example 1, except that the added amount of the lubricant was set to 1 part by weight.

Inventive example 3

A magnetic tape was prepared in accordance with the same manner as that in Inventive example 1, except that the added amount of the lubricant was set to 2 part by weight.

Inventive example 4

A magnetic tape was prepared in accordance with the same manner as that in Inventive example 1, except that the added amount of the lubricant was set to 3 part by weight.

For each of the magnetic tapes prepared in Inventive Examples 1 to 4, the lubricant in the organic thin film (magnetic layer) on the recording medium was subjected to qualitative analysis by the analysis apparatus shown in FIG. 3, and the content of the lubricant was subjected to quantitative analysis. Further, the lubricant in the recording medium (in the surface layer of the PET film, that is, in the uppermost layer portion of the film) was subjected to qualitative analysis and quantitative analysis by examining the areal intensity of the stretching vibration peak of $CH_2$. FIGS. 7 to 10 show infrared absorption spectra obtained in Inventive Examples 1 to 4. These graphs each show the result of measuring the profile of the lubricant in the depth direction of the magnetic tape.

In the analysis using the apparatus shown in FIG. 3, the reference R composed of the magnetic tape containing no lubricant was first analyzed and then the sample S composed of each of the magnetic tapes in Inventive examples 1 to 4 was analyzed. With such analysis, the infrared absorption spectrum of only the lubricant for each of the magnetic tapes in Inventive examples 1 to 4 is obtained. Further, since the molecular structure of the lubricant is determined before analysis by using the apparatus shown in FIG. 3, the lubricant can be qualitatively and quantitatively analyzed by examining the areal intensity of the peak of the absorption spectrum peculiar to the molecular structure of the lubricant.

Comparative Example 1

Figure 11:
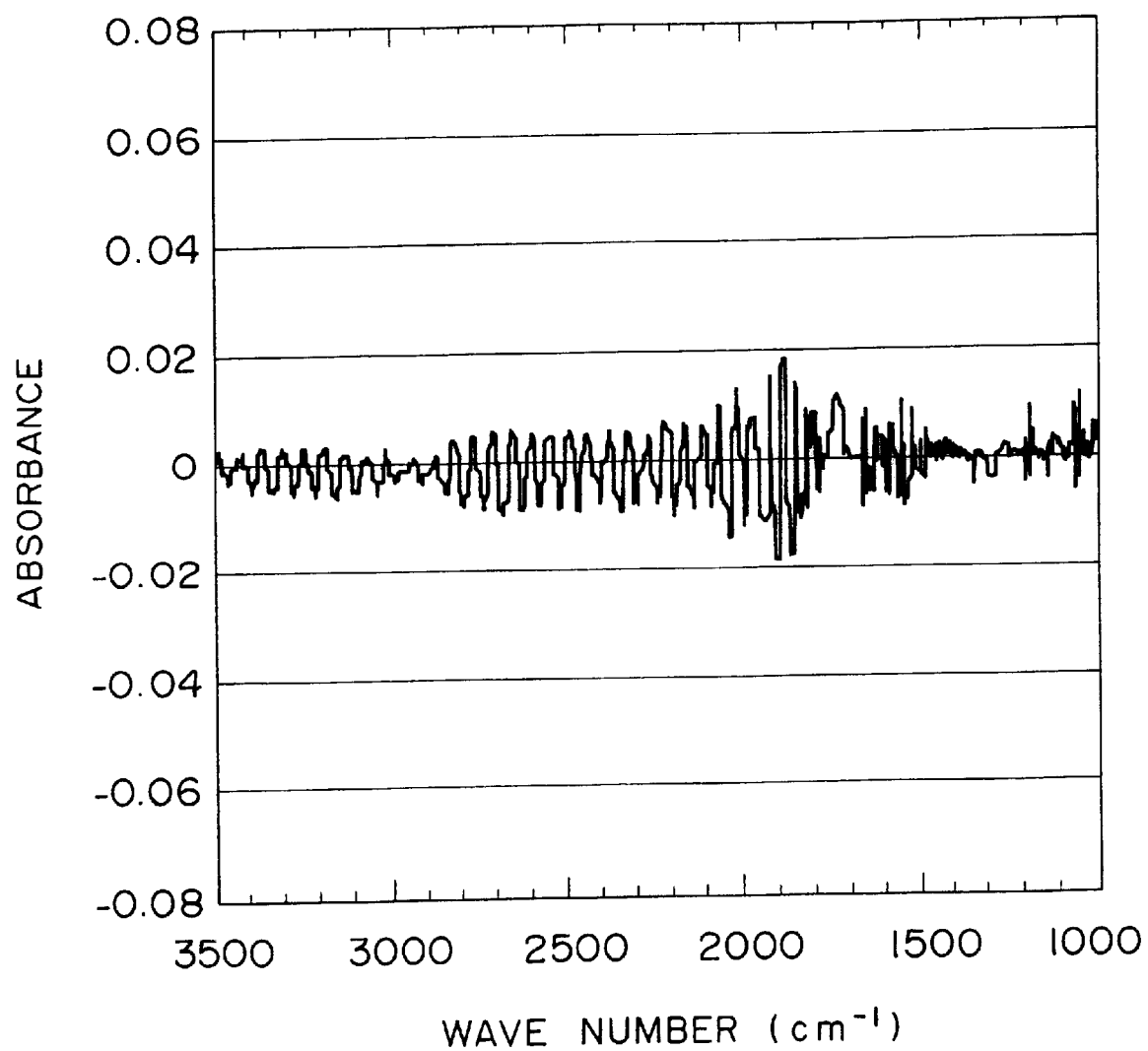
FIG. 11 is an infrared absorption spectrum obtained in Comparative Example 1.
Figure 13:
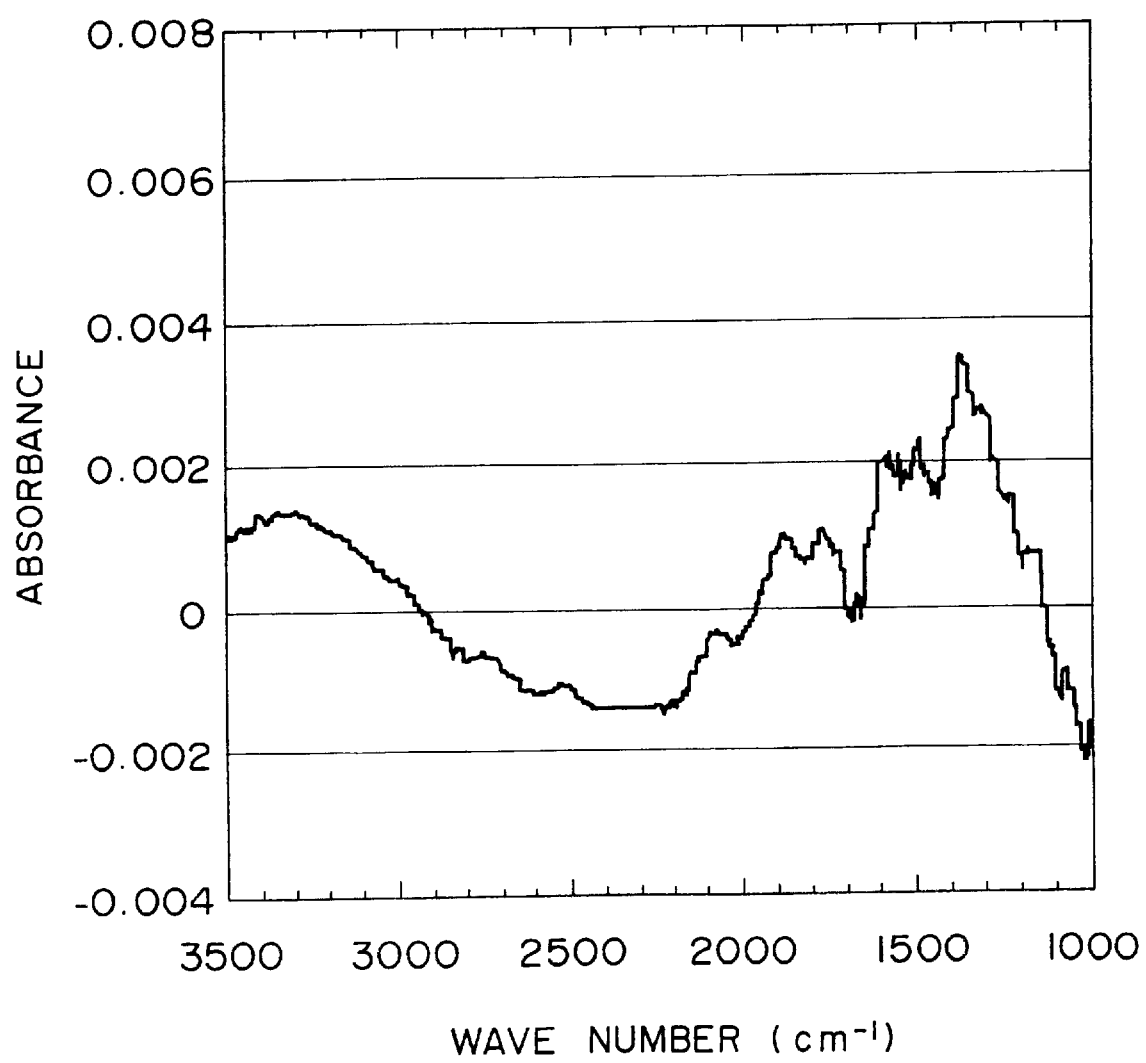
FIG. 13 is an infrared absorption spectrum obtained in Inventive Example 5 of the present invention.
Figure 14:
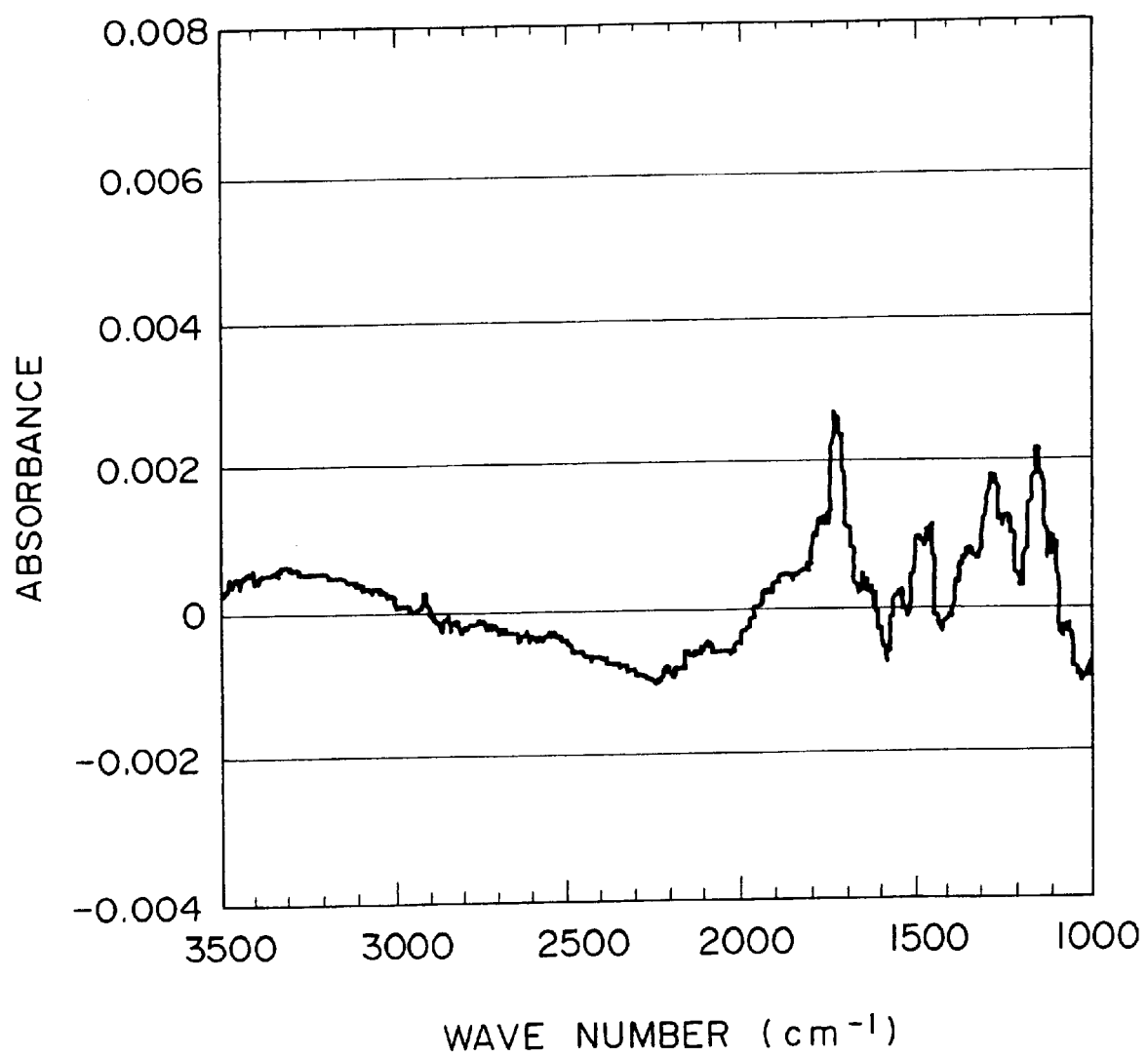
FIG. 14 is an infrared absorption spectrum obtained in Inventive Example 6 of the present invention.
Figure 15:
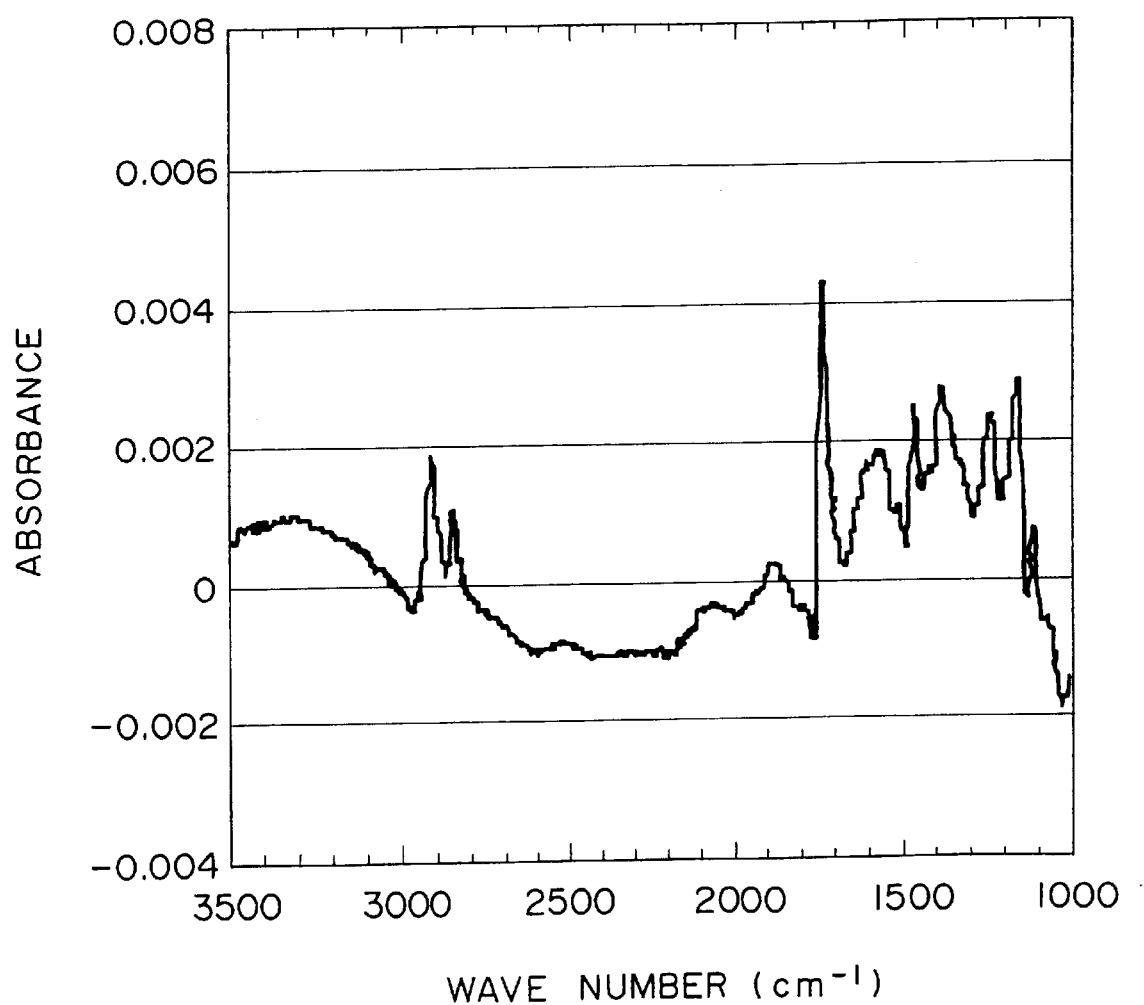
FIG. 15 is an infrared absorption spectrum obtained in Inventive Example 7 of the present invention.
Figure 16:
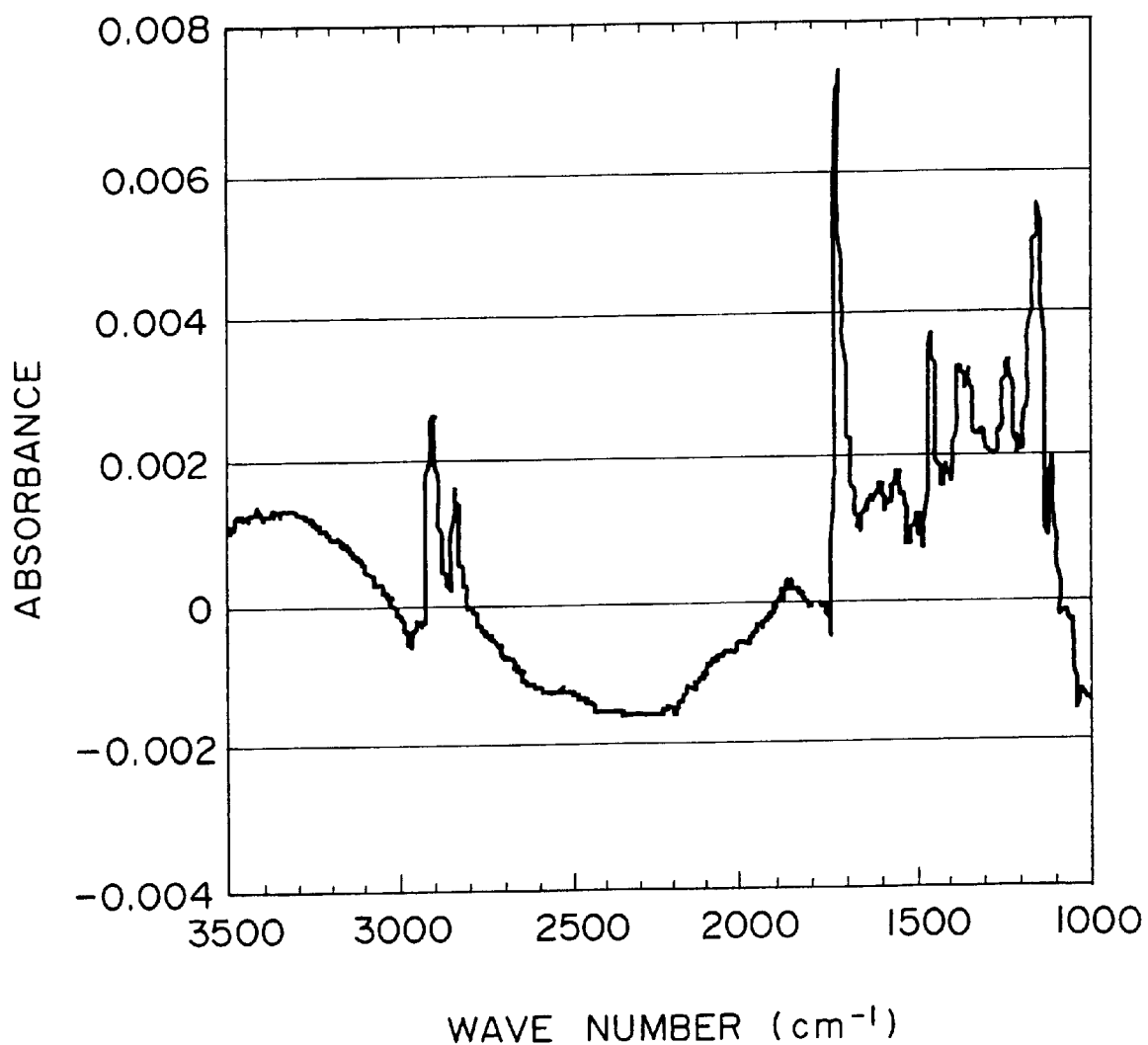
FIG. 16 is an infrared absorption spectrum obtained in Inventive Example 8 of the present invention.

With respect to the magnetic tape obtained in Inventive example 4, the absorption spectrum was obtained by the high sensitivity reflected infrared absorption spectroscopy. The result is shown in FIG. 11. As is apparent from FIG. 11, unlike the analysis method of the present invention, qualitative analysis and quantitative analysis for the lubricant was both impossible. The reason for this may be considered that, in the high sensitivity reflected infrared absorption spectroscopy, the infrared light ray passes through the sample and thereby the effect of interference of light becomes large and the reflectance of the sample becomes very small. On the contrary, according to the analysis method of the present invention, the infrared light ray travels only to the surface layer portion of the supporting body from the surface of the magnetic layer.

FIG. 12 shows the result of measuring the content of the lubricant in the magnetic layer at one specific point of each of the samples in Inventive Examples 1 to 4 by the apparatus shown in FIG. 3. In this graph, the abscissa designates the added amount of the lubricant in the magnetic paint, and the ordinate designates the measured content of the lubricant in the magnetic layer actually formed. The values, 0.5, 1, 2, 3 on the abscissa are the added amounts of the lubricant in the magnetic paints of the samples in Inventive Examples 1 to 4; while the values, about 0.5, 3, 60 and 80 on the ordinate are the contents of the lubricant in the magnetic layers of the samples in Inventive Examples 1 to 4. Accordingly, the ratio of the value (added amount of the lubricant in the magnetic paint) on the abscissa to the value (content of the lubricant in the magnetic layer) on the ordinate is substantially constant.

As is apparent from the spectra obtained in Comparative Example 1 (see FIG. 11), according to the high sensitivity reflected infrared absorption spectroscopy, the content of the lubricant in the magnetic layer cannot be measured at all. On the other hand, as is apparent from the above result shown in FIG. 12, according to the method using the analysis apparatus of the present invention, the content of the lubricant in the magnetic layer can be considerably accurately measured.

Inventive Examples 5 to 8

In each of these examples, a metal thin film type magnetic tape was prepared and was analyzed by using the apparatus shown in FIG. 3. To be more specific, a Co—Ni alloy was deposited on a PET film having a thickness of 10 μm by an oblique deposition method, to form a ferromagnetic metal thin film having a thickness of 100 nm. A carbon film having a thickness of 15 nm was deposited on the metal thin film by sputtering, and a solution obtained by dissolving a lubricant (heptyl stearate) at each of the following concentrations in toluene was applied to the carbon film. The film thus obtained was cut into a width of 8 mm, to form a sample tape.

The concentration of the lubricant in the toluene solution was set at 0.5 wt % for Inventive Example 5; 1 wt % for Inventive Example 6; 2 wt % for Inventive Example 7; and 3 wt % for Inventive Example 8. The infrared absorption spectra of the sample tapes measured by using the apparatus shown in FIG. 3 are shown in FIGS. 13 to 16.

Comparative Example 2

Figure 17:
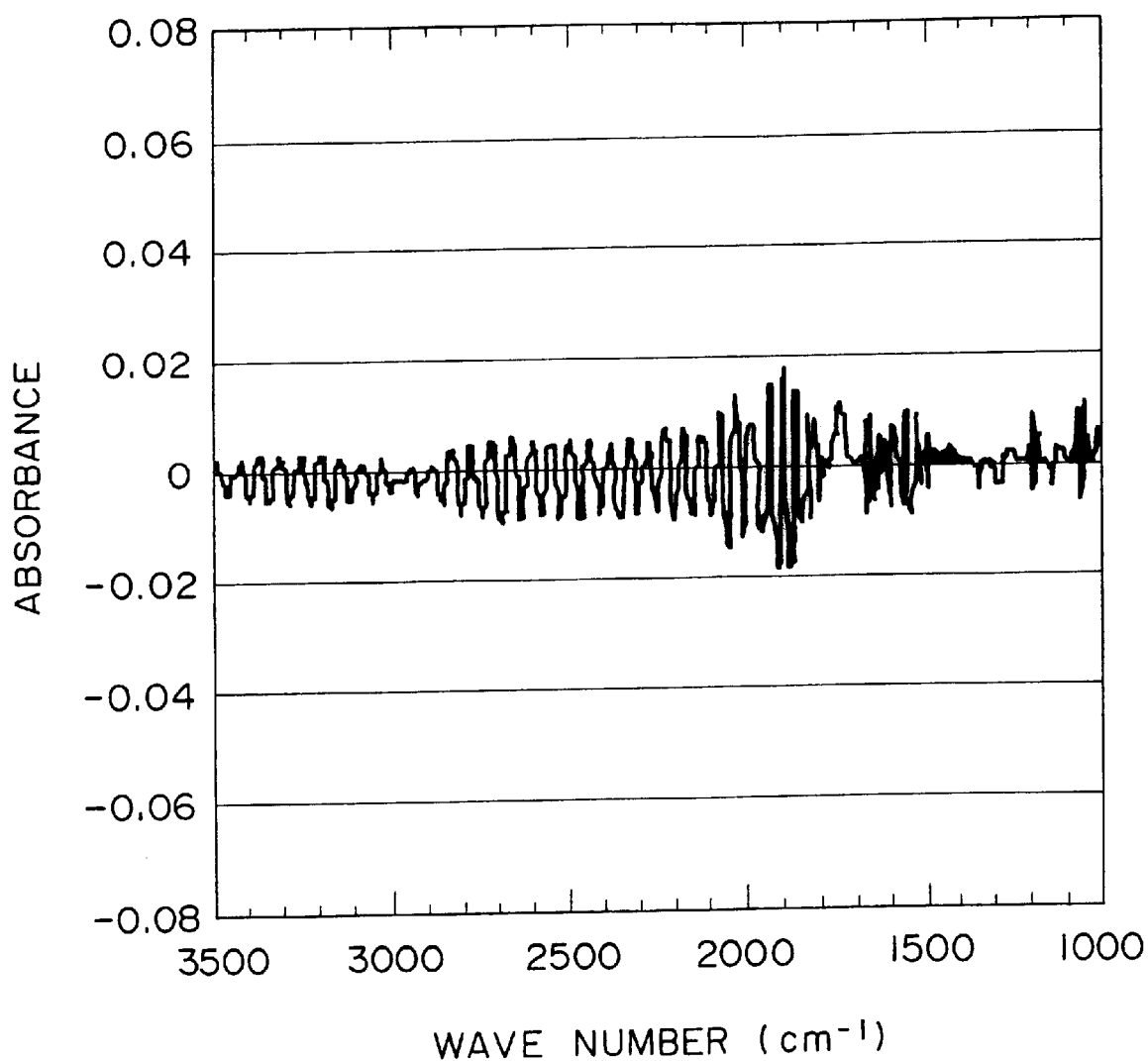
FIG. 17 is an infrared absorption spectrum obtained in Comparative Example 2.

The sample tape obtained in Inventive example 8 was analyzed by the high sensitivity reflected infrared absorption spectroscopy. The infrared absorption spectrum thus obtained is shown in FIG. 17. As is apparent from this graph, according to the high sensitivity reflected infrared absorption spectroscopy, the qualitative analysis and quantitative analysis for the lubricant were both impossible.

Inventive Example 9

Figure 18:
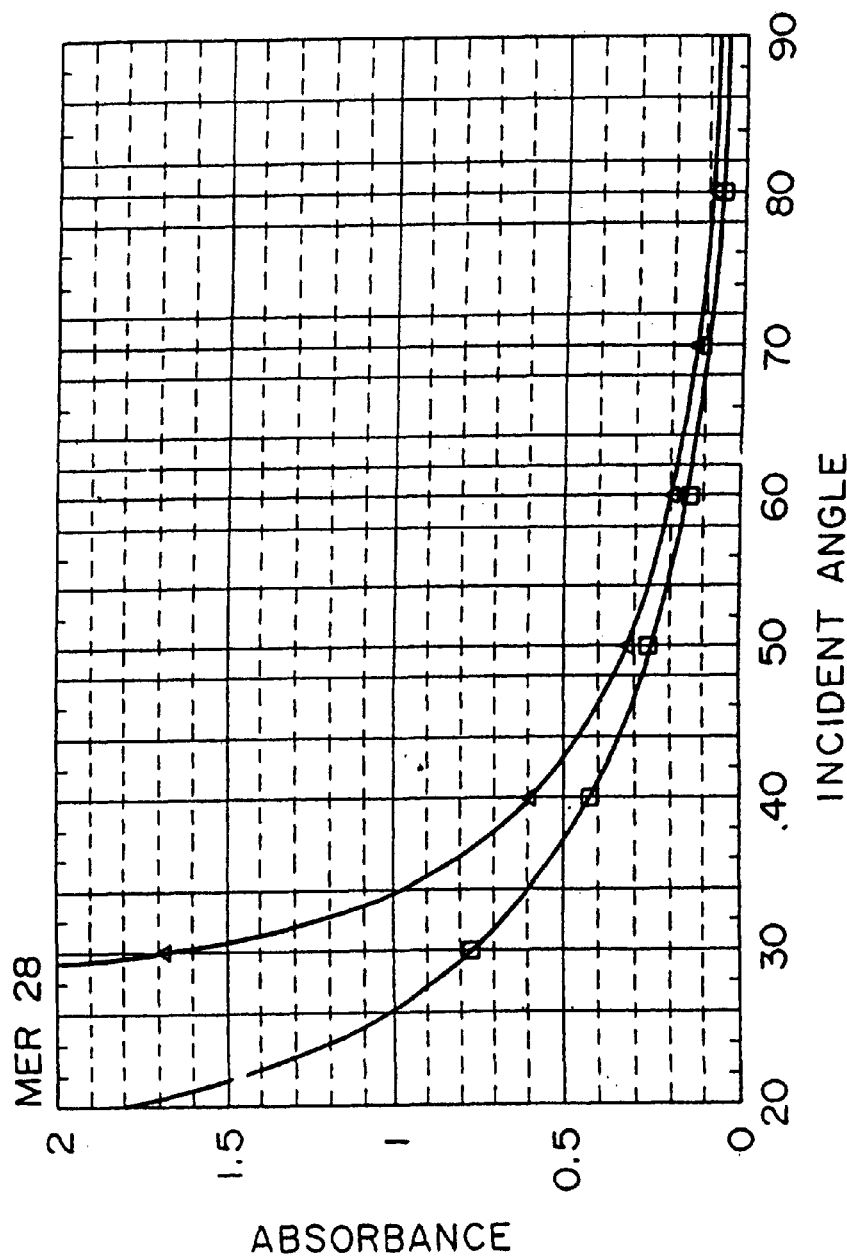
FIG. 18 is a graph showing a relationship between the incident angle of an infrared light ray incident on a sample in Inventive example 9 of the present invention and absorbances of specific function groups.

FIG. 18 is a graph showing the result of measuring the content of the lubricant in the magnetic layer of the sample obtained in Inventive Example 1 at a specific point of the sample by using the optical system shown in FIG. 1 while varying the incident angle of an infrared light ray. In this graph, the absorption of each of methylene and carbonyl in the lubricant varies depending on the change in incident angle of the infrared light ray, which corresponds to the above-described theoretical equation (1). Accordingly, it is apparent that the measured depth of the sample corresponds to the change in incident angle of the infrared light ray.

Figure 19:
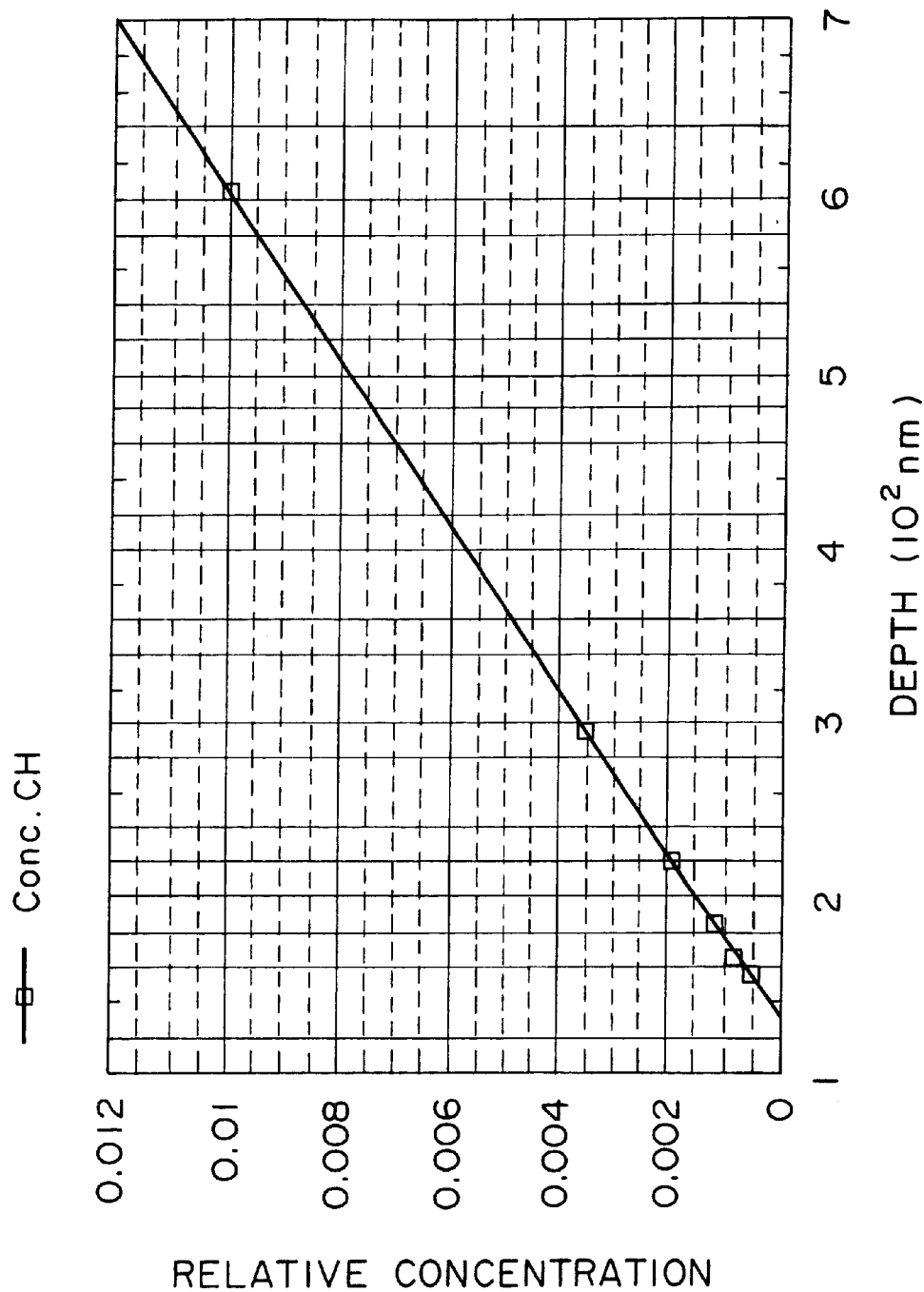
FIG. 19 is a graph showing a change in content (relative value) of a lubricant in the depth direction of the sample in Inventive example 9, obtained on the basis of the measured result shown in FIG. 18.

FIG. 19 is a graph showing a change in content (relative value) of the lubricant in the depth direction of the sample, obtained on the basis of the measured result shown in FIG. 18. In this sample, the content of the lubricant varies linearly in the depth direction of the sample. This means that the lubricant is uniformly distributed in the magnetic layer.

Additionally, in the above measurement, since the incident angle of the infrared light ray on the sample can be changed without opening/closing the sample chamber, it is not required to substitute the atmosphere in the sample chamber for nitrogen after change of the incident angle. As a result, it took only 15 min to measure the content of the lubricant at six points.

Comparative Example 3

In the case of using a commercial optical system (trade name SIEGAL, sold by Harrick, Co., Inc.), the substitution of the atmosphere in the sample chamber for nitrogen took 30 min. for each change in infrared light ray. As a result, it took 3 hr. to measure the content of the lubricant at six points.

As is apparent from the above description, the infrared microscopic/FT-IR apparatus or a method for analysis of a recording medium by using the apparatus exhibits the effect capable of simply performing qualitative analysis and quantitative analysis of an organic material, particularly, an organic lubricant of a surface portion (surface and a directly under portion of the surface) of a high density recording medium such as a magnetic tape, floppy disk, optical disk, or hard disk at a high accuracy and a high repeatability. Such an effect cannot be obtained by the related art high sensitivity reflected absorption spectroscopy or internally reflected infrared absorption spectroscopy.

While the embodiments of the present invention have been described using specific terms, such description is for illustrative purposes only, and it is to be understood that changes and variations may be made without departing from the spirit or scope of the following claims.

What is claimed is:

1. An infrared microscopic/FT-IR (Fourier transform infrared spectrometer) apparatus based on an attenuated total reflection method, said apparatus comprising:

a semi-spherical prism having a smooth, flat bottom surface; and an incident angle variable optical system in which a sample mounting portion is separated from an incident optical system by said semi-spherical prism; the incident angle variable optical system including first and second movable mirrors positioned in parallel with one another and mounted on a linearly movable stage;

wherein a surface portion of a sample is analyzed by bringing said prism in press-contact with the surface of the sample, making an infrared light ray incident on said prism at a specific angle, and analyzing the spectrum of the infrared light ray totally reflected from the surface of the sample by said FT-IR apparatus; and the specific angle of the infrared light ray incident on said prism is changed by linearly translating the movable stage.

2. An infrared microscopic/FT-IR apparatus according to claim 1, wherein said incident angle variable optical system is housed in an enclosed sample chamber.

3. An infrared microscopic/FT-IR apparatus according to claim 1, wherein said incident angle variable optical system comprises parabolic mirrors opposed to each other.

4. An infrared microscopic/FT-IR apparatus according to claim 1, further comprising:

a contact pressure control means for finely adjusting a contact pressure applied from the surface of the sample to said bottom surface of said semi-spherical prism.

5. An infrared microscopic/FT-IR apparatus according to claim 4 wherein said contact pressure is 10 kgf/cm$^2$ or less.

6. An infrared microscopic/FT-IR apparatus according to claim 4 wherein said contact pressure is uniform over a contact area.

7. An infrared microscopic/FT-IR apparatus according to claim 6 wherein said contact pressure control includes a pressure detecting mechanism.

8. An infrared microscopic/FT-IR apparatus according to claim 7 wherein said pressure detecting mechanism includes a piezoelectric sensor element.

9. An infrared microscopic/FT-IR apparatus based on an attenuated total reflection method, said apparatus comprising:

a semi-spherical prism having a smooth, flat bottom surface;

a contact pressure control means for finely adjusting a contact pressure applied from the surface of the sample to said bottom surface of said semi-spherical prism; and an incident angle variable optical system including first and second movable mirrors positioned in parallel with one another and mounted on a linearly movable stage;

wherein a surface portion of a sample is analyzed by bringing said prism in press-contact with the surface of the sample, making an infrared light ray incident on said prism at a specific angle, and analyzing the spectrum of the infrared light ray totally reflected from the surface of the sample by said FT-IR apparatus; and the specific angle of the infrared light ray incident on said prism is changed by linearly translating the movable stage.

10. An infrared microscopic/FT-IR apparatus according to claim 9 wherein said contact pressure is 10 kgf/cm$^2$ or less.

11. An infrared microscopic/FT-IR apparatus according to claim 9 wherein said contact pressure is uniform over a contact area.

12. An infrared microscopic/FT-IR apparatus according to claim 11 wherein said contact pressure control includes a pressure detecting mechanism.

13. An infrared microscopic/FT-IR apparatus according to claim 12 wherein said pressure detecting mechanism includes a piezoelectric sensor element.

14. A method for carrying out at least one of qualitative analysis and quantitative analysis for a surface portion of a recording medium, comprising:

preparing an infrared microscopic/FT-IR apparatus based on an attenuated total reflection method, said apparatus including a semi-spherical prism having a smooth, flat bottom surface, and an incident angle variable optical system in which a sample mounting portion is separated from an incident optical system by said semi-spherical prism, the incident angle variable optical system including first and second movable mirrors positioned in parallel with one another and mounted on a linearly movable stage;

bringing said prism in press-contact with the surface of the sample;

making an infrared light ray incident on said prism at a specific angle;

adjusting the specific angle by linearly translating the movable stage; and analyzing the spectrum of the light ray totally reflected from the surface of the sample by said FT-IR apparatus.

15. A method for carrying out at least one of qualitative analysis and quantitative analysis for a surface portion of a recording medium, comprising:

preparing an infrared microscopic/FT-IR apparatus based on an attenuated total reflection method, said apparatus including a semi-spherical prism having a smooth, flat bottom surface, a contact pressure control means for finely adjusting a contact pressure applied from the surface of the sample to said bottom surface of said semi-spherical prism, and an incident angle variable optical system including first and second movable mirrors positioned in parallel with one another and mounted on a linearly movable stage;

bringing said prism in press-contact with the surface of the sample;

making an infrared light ray incident on said prism at a specific angle;

adjusting the specific angle by linearly translating the movable stage; and analyzing the spectrum of the light ray totally reflected from the surface of the sample by said FT-IR apparatus.

16. A method according to claim 14 or 15, wherein said recording medium is a coating type magnetic recording medium in which a magnetic layer is formed on a non-magnetic supporting body by a coating film mainly containing a ferromagnetic powder and a binder and additionally containing an organic lubricant.

17. A method according to claim 14 or 15, wherein said recording medium is a metal thin film type magnetic recording medium in which a metal thin is formed on a non-magnetic supporting body and a magnetic layer containing an organic lubricant is formed on said metal thin film.

18. A method according to claim 14 or 15, wherein said recording medium is a metal thin film optical recording medium in which an optical recording layer is formed on a non-magnetic supporting body and an organic thin film containing an organic lubricant is formed on the surface of said optical recording layer.

19. A method according to claim 14 or 15, wherein an infrared light ray having a wavelength ranging from 2 $\mu$m to 20 $\mu$m is made incident on said prism.

20. A method according to claim 14 or 15, wherein said semi-spherical prism has a refractive-index ranging from 2.0 to 4.0.

* * * * *